(12) United States Patent
Gill et al.

(10) Patent No.: US 10,240,167 B2
(45) Date of Patent: *Mar. 26, 2019

(54) CRISPR ENABLED MULTIPLEXED GENOME ENGINEERING

(71) Applicant: THE REGENTS OF THE UNIVERSITY OF COLORADO, A BODY CORPORATE, Denver, CO (US)

(72) Inventors: Ryan T. Gill, Denver, CO (US); Andrew Garst, Boulder, CO (US)

(73) Assignee: Inscripta, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/948,789

(22) Filed: Apr. 9, 2018

(65) Prior Publication Data

US 2018/0230493 A1 Aug. 16, 2018

Related U.S. Application Data

(63) Continuation of application No. 15/630,909, filed on Jun. 22, 2017, now Pat. No. 9,982,278, which is a continuation of application No. 15/116,616, filed as application No. PCT/US2015/015476 on Feb. 11, 2015.

(60) Provisional application No. 61/938,608, filed on Feb. 11, 2014.

(51) Int. Cl.
| | |
|---|---|
| C12N 15/90 | (2006.01) |
| C12N 15/10 | (2006.01) |
| C12N 9/22 | (2006.01) |
| C12N 15/11 | (2006.01) |
| C40B 40/08 | (2006.01) |

(52) U.S. Cl.
CPC ............. *C12N 15/902* (2013.01); *C12N 9/22* (2013.01); *C12N 15/102* (2013.01); *C12N 15/1024* (2013.01); *C12N 15/1082* (2013.01); *C12N 15/1093* (2013.01); *C12N 15/11* (2013.01); *C12N 15/111* (2013.01); *C40B 40/08* (2013.01); *C12N 2310/10* (2013.01); *C12N 2310/20* (2017.05); *C12N 2320/11* (2013.01); *C12N 2320/12* (2013.01); *C12N 2330/31* (2013.01)

(58) Field of Classification Search
None
See application file for complete search history.

(56) References Cited

U.S. PATENT DOCUMENTS

| | | | |
|---|---|---|---|
| 8,153,432 B2 | 4/2012 | Church et al. | |
| 8,569,041 B2 | 10/2013 | Church et al. | |
| 8,906,616 B2 | 12/2014 | Zhang et al. | |
| 9,982,278 B2 | 5/2018 | Gill et al. | |
| 10,017,760 B2 | 7/2018 | Gill et al. | |
| 2010/0034924 A1 | 2/2010 | Fremaux et al. | |
| 2014/0068797 A1 | 3/2014 | Doudna et al. | |
| 2014/0089681 A1 | 3/2014 | Goto et al. | |
| 2014/0199767 A1 | 7/2014 | Barrangou et al. | |
| 2014/0273226 A1 | 9/2014 | Wu et al. | |
| 2014/0273232 A1 | 9/2014 | Zhang et al. | |
| 2014/0295557 A1 | 10/2014 | Joung et al. | |
| 2015/0031133 A1 | 1/2015 | Church et al. | |
| 2015/0031134 A1 | 1/2015 | Zhang et al. | |
| 2015/0064138 A1 | 3/2015 | Lu et al. | |
| 2015/0079680 A1 | 3/2015 | Bradley et al. | |
| 2015/0098954 A1 | 4/2015 | Hyde et al. | |
| 2015/0133315 A1 | 5/2015 | Jacobson et al. | |
| 2015/0159174 A1 | 6/2015 | Frendewey et al. | |
| 2015/0176013 A1 | 6/2015 | Musunuru et al. | |
| 2015/0201634 A1 | 7/2015 | Fremaux et al. | |
| 2015/0225773 A1 | 8/2015 | Farmer et al. | |
| 2015/0247150 A1 | 9/2015 | Zhang et al. | |
| 2015/0353905 A1 | 12/2015 | Weiss et al. | |
| 2015/0353917 A1 | 12/2015 | Miller | |
| 2016/0024523 A1 | 1/2016 | Joung et al. | |
| 2016/0024529 A1 | 1/2016 | Carstens | |
| 2016/0053272 A1 | 2/2016 | Wurtzel et al. | |
| 2016/0053304 A1 | 2/2016 | Wurtzel et al. | |
| 2016/0060653 A1 | 3/2016 | Doudna et al. | |
| 2016/0060654 A1 | 3/2016 | Doudna et al. | |
| 2016/0068864 A1 | 3/2016 | Doudna et al. | |
| 2016/0076093 A1 | 3/2016 | Shendure et al. | |
| 2016/0102322 A1 | 4/2016 | Ravinder et al. | |
| 2016/0115488 A1 | 4/2016 | Zhang et al. | |
| 2016/0115489 A1 | 4/2016 | Zhang et al. | |
| 2016/0160210 A1 | 6/2016 | Mali et al. | |
| 2016/0168592 A1 | 6/2016 | Church et al. | |
| 2016/0186168 A1 | 6/2016 | Konieczka et al. | |
| 2016/0264995 A1 | 9/2016 | Yamamoto et al. | |
| 2016/0289673 A1 | 10/2016 | Huang et al. | |
| 2016/0289675 A1 | 10/2016 | Ryan et al. | |
| 2016/0298134 A1 | 10/2016 | Chen et al. | |
| 2016/0298135 A1 | 10/2016 | Chen et al. | |
| 2016/0298138 A1 | 10/2016 | Chen et al. | |
| 2016/0367702 A1 | 12/2016 | Hoge et al. | |
| 2017/0002339 A1 | 1/2017 | Barrangou et al. | |
| 2017/0044569 A9 | 2/2017 | Church et al. | |

(Continued)

FOREIGN PATENT DOCUMENTS

| | | | |
|---|---|---|---|
| EP | 2764103 A2 | 8/2014 | |
| EP | 2825654 A1 | 1/2015 | |

(Continued)

OTHER PUBLICATIONS

Agresti, et al. Ultrahigh-throughput screening in drop-based microfluidics for directed evolution. Proc Natl Acad Sci U S A. Mar. 2, 2010;107(9):4004-9. doi: 10.1073/pnas.0910781107. Epub Feb. 8, 2010.

(Continued)

*Primary Examiner* — Nancy J Leith
(74) *Attorney, Agent, or Firm* — Wilson Sonsini Goodrich & Rosati

(57) ABSTRACT

Described herein are methods and vectors for rational, multiplexed manipulation of chromosomes within open reading frames (e.g., in protein libraries) or any segment of a chromosome in a cell or population of cells, in which various CRISPR systems are used.

34 Claims, 19 Drawing Sheets

Specification includes a Sequence Listing.

(56) References Cited

U.S. PATENT DOCUMENTS

| | | |
|---|---|---|
| 2017/0051276 A1 | 2/2017 | May et al. |
| 2017/0051310 A1 | 2/2017 | Doudna et al. |
| 2017/0051311 A1 | 2/2017 | Dalia et al. |
| 2017/0073705 A1 | 3/2017 | Chen et al. |
| 2017/0080107 A1 | 3/2017 | Chivukula et al. |
| 2017/0114334 A1 | 4/2017 | May et al. |
| 2017/0145425 A1 | 5/2017 | Kim et al. |
| 2017/0191123 A1 | 7/2017 | Kim et al. |
| 2017/0204407 A1 | 7/2017 | Gilbert et al. |
| 2017/0233752 A1 | 8/2017 | Shiboleth et al. |
| 2017/0240922 A1 | 8/2017 | Gill et al. |
| 2017/0321226 A1 | 11/2017 | Gill et al. |
| 2017/0369870 A1 | 12/2017 | Gill et al. |
| 2018/0230460 A1 | 8/2018 | Gill et al. |
| 2018/0230492 A1 | 8/2018 | Gill et al. |

FOREIGN PATENT DOCUMENTS

| | | |
|---|---|---|
| EP | 2828386 A1 | 1/2015 |
| EP | 2840140 A1 | 2/2015 |
| EP | 2848690 A1 | 3/2015 |
| EP | 2898075 A1 | 7/2015 |
| EP | 3009511 A2 | 4/2016 |
| EP | 2840140 B1 | 11/2016 |
| EP | 3144390 A1 | 3/2017 |
| WO | WO-2007144770 A2 | 12/2007 |
| WO | WO-2012142591 A2 | 10/2012 |
| WO | WO-2013176772 A1 | 11/2013 |
| WO | WO-2013176915 A1 | 11/2013 |
| WO | WO-2014022702 A2 | 2/2014 |
| WO | WO-2014065596 A1 | 5/2014 |
| WO | WO-2014093595 A1 | 6/2014 |
| WO | WO-2014093622 A2 | 6/2014 |
| WO | WO-2014093661 A2 | 6/2014 |
| WO | WO-2014099744 A1 | 6/2014 |
| WO | WO-2014110006 A1 | 7/2014 |
| WO | WO-2014143381 A1 | 9/2014 |
| WO | WO-2014150624 A1 | 9/2014 |
| WO | WO-2014191128 A1 | 12/2014 |
| WO | WO-2015006290 A1 | 1/2015 |
| WO | WO-2015006747 A2 | 1/2015 |
| WO | WO-2015013583 A2 | 1/2015 |
| WO | WO-2015017866 A1 | 2/2015 |
| WO | WO-2015048577 A2 | 4/2015 |
| WO | WO-2015048690 A1 | 4/2015 |
| WO | WO-2015068785 A1 | 5/2015 |
| WO | WO-2015069682 A2 | 5/2015 |
| WO | WO-2015070062 A1 | 5/2015 |
| WO | WO-2015071474 A2 | 5/2015 |
| WO | WO-2015089354 A1 | 6/2015 |
| WO | WO-2015123339 A1 | 8/2015 |
| WO | WO-2015153889 A2 | 10/2015 |
| WO | WO-2015159086 A1 | 10/2015 |
| WO | WO-2015159087 A1 | 10/2015 |
| WO | WO-2015179540 A1 | 11/2015 |
| WO | WO-2015191693 A2 | 12/2015 |
| WO | WO-2015195798 A1 | 12/2015 |
| WO | WO-2015198020 A1 | 12/2015 |
| WO | WO-2015191693 A3 | 2/2016 |
| WO | WO-2016040594 A1 | 3/2016 |
| WO | WO-2016070037 A2 | 5/2016 |
| WO | WO-2016099887 A1 | 6/2016 |
| WO | WO-2016100955 A2 | 6/2016 |

OTHER PUBLICATIONS

Alper, et al. Engineering yeast transcription machinery for improved ethanol tolerance and production. Science. Dec. 8, 2006;314(5805):1565-8.

Alper, et al. Global transcription machinery engineering: a new approach for improving cellular phenotype. Metab Eng. May 2007;9(3):258-67. Epub Jan. 8, 2007.

Baba, et al. Construction of Escherichia coli K-12 in-frame, single-gene knockout mutants: the Keio collection. Mol Syst Biol. 2006;2:2006.0008. Epub Feb. 21, 2006.

Bakan, et al. ProDy: protein dynamics inferred from theory and experiments. Bioinformatics. Jun. 1, 2011;27(11):1575-7. doi: 10.1093/bioinformatics/btr168. Epub Apr. 5, 2011.

Basak, et al. Enhancing E. coli tolerance towards oxidative stress via engineering its global regulator cAMP receptor protein (CRP). PLoS One. 2012;7(12):e51179. doi: 10.1371/journal.pone.0051179. Epub Dec. 14, 2012.

Bhabha, et al. Divergent evolution of protein conformational dynamics in dihydrofolate reductase. Nat Struct Mol Biol. Nov. 2013;20(11):1243-9. doi: 10.1038/nsmb.2676. Epub Sep. 29, 2013.

Bhaya et al. CRISPR-Cas systems in bacteria and archaea: versatile small RNAs for adaptive defense and regulation. Annu Rev Genet 45:273-297 (2011).

Bikard et al. CRiSPR interference can prevent natural transformation and virulence acquisition during in vivo bacterial infection. Cell Host & Microbe 12(2):177-186 (2012).

Brouns, et al. Small CRISPR RNAs guide antiviral defense in prokaryotes. Science. Aug. 15, 2008;321(5891):960-4. doi: 10.1126/science.1159689.

Chang, et al. Structural systems biology evaluation of metabolic thermotolerance in Escherichia coli. Science. Jun. 7, 2013;340(6137):1220-3. doi: 10.1126/science.1234012.

Chen, et al. Genome-wide CRISPR screen in a mouse model of tumor growth and metastasis. Cell. Mar. 12, 2015;160(6):1246-60. doi: 10.1016/j.cell.2015.02.038. Epub 2015 Mar. 5, 2015.

Cong, et al. Multiplex genome engineering using CRISPR/Cas systems. Science. Feb. 15, 2013;339(6121):819-23. doi: 10.1126/science.1231143. Epub Jan. 3, 2013.

Costantino, et al. Enhanced levels of lambda Red-mediated recombinants in mismatch repair mutants. Proc Natl Acad Sci U S A. Dec. 23, 2003;100(26):15748-53. Epub Dec. 12, 2003.

Datta, et al. A set of recombineering plasmids for gram-negative bacteria. Gene. Sep. 1, 2006;379:109-15. Epub May 4, 2006.

Dicarlo, et al. Genome engineering in Saccharomyces cerevisiae using CRISPR-Cas systems. Nucleic Acids Res. Apr. 2013;41(7):4336-43. doi: 10.1093/nar/gkt135. Epub Mar. 4, 2013.

"Dickinson et al. Engineering the Caenorhabditis elegans Genome Using Cas9-Triggered Homologous Recombination; Nat Methods. Oct. 2013; 10(10): 1028-1034; doi: 10.1038/nmeth.2641".

European Search Report dated Jun. 26, 2017 for EP Application No. 15749644.9.

Examination Report dated Jun. 27, 2017 for GB Application No. 1615434.6.

Findlay, et al. Saturation editing of genomic regions by multiplex homology-directed repair. Nature. Sep. 4, 2014;513(7516):120-3. doi: 10.1038/nature13695.

Firth, et al. GLUE-IT and PEDEL-AA: new programmes for analyzing protein diversity in randomized libraries. Nucleic Acids Res. Jul. 1, 2008;36(Web Server issue):W281-5. doi: 10.1093/nar/gkn226. Epub Apr. 28, 2008.

Fisher, et al. Enhancing tolerance to short-chain alcohols by engineering the Escherichia coli AcrB efflux pump to secrete the non-native substrate n-butanol. ACS Synth Biol. Jan. 17, 2014;3(1):30-40. doi: 10.1021/sb400065q. Epub Sep. 13, 2013.

Foo, et al. Directed evolution of an E. coli inner membrane transporter for improved efflux of biofuel molecules. Biotechnol Biofuels. May 21, 2013;6(1):81. doi: 10.1186/1754-6834-6-81.

Glebes, et al. Comparison of genome-wide selection strategies to identify furfural tolerance genes in Escherichia coli. Biotechnol Bioeng. Jan. 2015;112(1):129-40. doi: 10.1002/bit.25325. Epub Sep. 2, 2014.

Hamady, et al. Error-correcting barcoded primers for pyrosequencing hundreds of samples in multiplex. Nat Methods. Mar. 2008;5(3):235-7. doi: 10.1038/nmeth.1184. Epub Feb. 10, 2008.

Hsu, et al., DNA targeting specificity of RNA-guided Cas9 nucleases. Nature Biotechnology. Jul. 21, 2013; 31(9): 827-834.

Hwang, et al. Efficient genome editing in zebrafish using a CRISPR-Cas system. Nat Biotechnol. Mar. 2013;31(3):227-9. doi: 10.1038/nbt.2501. Epub Jan. 29, 2013.

(56) References Cited

OTHER PUBLICATIONS

Ibanez, et al. Mass spectrometry-based metabolomics of single yeast cells. Proc Natl Acad Sci U S A. May 28, 2013;110(22):8790-4. doi: 10.1073/pnas.1209302110. Epub May 13, 2013.
International search report and written opinion dated Jul. 28, 2015 for PCT/US2015/015476.
Isaacs, et al. Precise manipulation of chromosomes in vivo enables genome-wide codon replacement. Science. Jul. 15, 2011;333(6040):348-53. doi: 10.1126/science.1205822.
Iwakura, et al. Evolutional design of a hyperactive cysteine- and methionine-free mutant of *Escherichia coli* dihydrofolate reductase. J Biol Chem. May 12, 2006;281(19):13234-46. Epub Mar. 1, 2006.
Jiang, et al. Multigene editing in the *Escherichia coli* genome via the CRISPR-Cas9 system. Appl Environ Microbiol. Apr. 2015;81(7):2506-14. doi: 10.1128/AEM.04023-14. Epub Jan. 30, 2015.
Jiang et al. RNA-guided editing of bacterial genomes using CRISPR-Cas systems. Nat Biotechnol 31:233-239 (2013).
Jinek, et al. A programmable dual-RNA-guided DNA endonuclease in adaptive bacterial immunity. Science. Aug. 17, 2012;337(6096):816-21. doi: 10.1126/science.1225829. Epub Jun. 28, 2012.
Kersten, et al. A mass spectrometry-guided genome mining approach for natural product peptidogenomics. Nat Chem Biol. Oct. 9, 2011;7(11):794-802. doi: 10.1038/nchembio.684.
Kim, et al. A guide to genome engineering with programmable nucleases. Nat Rev Genet. May 2014;15(5):321-34. doi: 10.1038/nrg3686. Epub Apr. 2, 2014.
Kim, et al. Hybrid restriction enzymes: zinc finger fusions to Fok I cleavage domain. Proc Natl Acad Sci U S A. Feb. 6, 1996;93(3):1156-60.
Kohanski, et al. A common mechanism of cellular death induced by bactericidal antibiotics. Cell. Sep. 7, 2007;130(5):797-810.
Kosuri, et al. Scalable gene synthesis by selective amplification of DNA pools from high-fidelity microchips. Nat Biotechnol. Dec. 2010;28(12):1295-9. doi: 10.1038/nbt.1716. Epub Nov. 28, 2010.
Lajoie, et al. Genomically recoded organisms expand biological functions. Science. Oct. 18, 2013;342(6156):357-60. doi: 10.1126/science.1241459.
Li, et al. Identification of factors influencing strand bias in oligonucleotide-mediated recombination in *Escherichia coli*. Nucleic Acids Res. Nov. 15, 2003;31(22):6674-87.
Makarova et al. An updated evolutionary classification of CRISPR-Cas systems. Nat Rev Microbiol 13:722-736 (2015).
Makarova, et al. Evolution and classification of the CRISPR-Cas systems. Nat Rev Microbiol. Jun. 2011;9(6):467-77. doi: 10.1038/nrmicro2577. Epub May 9, 2011.
Mali, et al. RNA-guided human genome engineering via Cas9. Science. Feb. 15, 2013;339(6121):823-6. doi: 10.1126/science.1232033. Epub Jan. 3, 2013.
Neylon, Cameron., Chemical and biochemical strategies for the randomization of protein encoding DNA sequences: library construction methods for directed evolution. Nucleic Acids Research, 2004, vol. 32, No. 4. 1448-1459.
Oh et al. CRISPR-Cas9-assisted recombineering in lactobacillus reuteri. Nucleic Acids Res 42(17):e131 (2014).
Pines, et al. Codon compression algorithms for saturation mutagenesis. ACS Synth Biol. May 15, 2015;4(5):604-14. doi: 10.1021/sb500282v. Epub Oct. 30, 2014.
Prior, et al. Broad-host-range vectors for protein expression across gram negative hosts. Biotechnol Bioeng. Jun. 1, 2010;106(2):326-32. doi: 10.1002/bit.22695.
Qi et al. Repurposing CRISPR as an RNA-guided platform for sequence-specific control of gene expression. Cell 152:1173-1183 (2013).
Raman, et al. Evolution-guided optimization of biosynthetic pathways. Proc Natl Acad Sci U S A. Dec. 16, 2014;111(50):17803-8. doi: 10.1073/pnas.1409523111. Epub Dec. 1, 2014.
Rodriguez-Verdugo, et al. Evolution of *Escherichia coli* rifampicin resistance in an antibiotic-free environment during thermal stress. BMC Evol Biol. Feb. 22, 2013;13:50. doi: 10.1186/1471-2148-13-50.
Sandoval, et al. Strategy for directing combinatorial genome engineering in *Escherichia coli*. Proc Natl Acad Sci U S A. Jun. 26, 2012;109(26):10540-5. doi: 10.1073/pnas.1206299109. Epub Jun. 11, 2012.
Sawitzke, et al. Probing cellular processes with oligo-mediated recombination and using the knowledge gained to optimize recombineering. J Mol Biol. Mar. 18, 2011;407(1):45-59. doi: 10.1016/j.jmb.2011.01.030. Epub Jan. 19, 2011.
Semenova et al. Interference by clustered regularly interspaced short palindromic repeat (CRISPR) RNA is governed by a seed sequence. PNAS USA 108(25):10098-10103 (2011).
Shalem, et al. Genome-scale CRISPR-Cas9 knockout screening in human cells. Science. Jan. 3, 2014;343(6166):84-7. doi: 10.1126/science.1247005. Epub Dec. 12, 2013.
Shendure. Life after genetics. Genome Med. Oct. 29, 2014;6(10):86. doi: 10.1186/s13073-014-0086-2. eCollection 2014.
Shmakov et al. Discovery and Functional Characterization of Diverse Class 2 CRISPR-Cas Systems. Mol Cell 60(3):385-397 (2015).
Smanski, et al. Functional optimization of gene clusters by combinatorial design and assembly. Nat Biotechnol. Dec. 2014;32(12):1241-9. doi: 10.1038/nbt.3063. Epub Nov. 24, 2014.
Stoebel, et al. Compensatory evolution of gene regulation in response to stress by *Escherichia coli* lacking RpoS. PLoS Genet. Oct. 2009;5(10):e1000671. doi: 10.1371/journal.pgen.1000671. Epub Oct. 2, 2009.
Swarts, et al. DNA-guided DNA interference by a prokaryotic Argonaute. Nature. Mar. 13, 2014;507(7491):258-61. doi: 10.1038/nature12971. Epub Feb. 16, 2014.
Tenaillon, et al. The molecular diversity of adaptive convergence. Science. Jan. 27, 2012;335(6067):457-61. doi: 10.1126/science.1212986.
Toprak, et al. Evolutionary paths to antibiotic resistance under dynamically sustained drug selection. Nat Genet. Dec. 18, 2011;44(1):101-5. doi: 10.1038/ng.1034.
Waaijers, et al. CRISPR/Cas9-targeted mutagenesis in Caenorhabditis elegans. Genetics. Nov. 2013;195(3):1187-91. doi: 10.1534/genetics.113.156299. Epub Aug. 26, 2013.
Wang, et al. Engineering furfural tolerance in *Escherichia coli* improves the fermentation of lignocellulosic sugars into renewable chemicals. Proc Natl Acad Sci U S A. Mar. 5, 2013;110(10):4021-6. doi: 10.1073/pnas.1217958110. Epub Feb. 19, 2013.
Wang, et al. Genome-scale promoter engineering by coselection MAGE. Nat Methods. Jun. 2012;9(6):591-3. doi: 10.1038/nmeth.1971. Epub Apr. 8, 2012.
Wang, et al. Multiplexed in vivo His-tagging of enzyme pathways for in vitro single-pot multienzyme catalysis. ACS Synth Biol. Feb. 17, 2012;1(2):43-52.
Wang, et al. One-step generation of mice carrying mutations in multiple genes by CRISPR/Cas-mediated genome engineering. Cell. May 9, 2013;153(4):910-8. doi: 10.1016/j.cell.2013.04.025. Epub May 2, 2013.
Wang, et al. Programming cells by multiplex genome engineering and accelerated evolution. Nature. Aug. 13, 2009;460(7257):894-8. doi: 10.1038/nature08187. Epub Jul. 26, 2009.
Warner, et al. Rapid profiling of a microbial genome using mixtures of barcoded oligonucleotides. Nat Biotechnol. Aug. 2010;28(8):856-62. doi: 10.1038/nbt.1653. Epub Jul. 18, 2010.
Watson, et al. Directed evolution of trimethoprim resistance in *Escherichia coli*. FEBS J. May 2007;274(10):2661-71. Epub Apr. 19, 2007.
"Withers, et al.Identification of isopentenol biosynthetic genes from Bacillus subtilis by a screening method based on isoprenoid precursor toxicity. Appl Environ Microbiol. Oct. 2007;73(19):6277-83. Epub Aug. 10, 2007."
Wolfe. The acetate switch. Microbiol Mol Biol Rev. Mar. 2005;69(1):12-50.

(56) References Cited

OTHER PUBLICATIONS

Zhang, et al., Efficient editing of malaria parasite genome using the CRISPR/Cas9 system. mBio. Jul. 2014; vol. 5 Art. e01414-14.

Zheng, et al. Metabolic engineering of *Escherichia coli* for high-specificity production of isoprenol and prenol as next generation of biofuels. Biotechnol Biofuels. Apr. 24, 2013;6:57. doi: 10.1186/1754-6834-6-57. eCollection 2013.

Office Action dated Nov. 8, 2017 for U.S. Appl. No. 15/630,909.

U.S. Appl. No. 15/630,909 Notice of Allowance dated Mar. 26, 2018.

U.S. Appl. No. 15/116,616 Office Action dated Mar. 16, 2018.

U.S. Appl. No. 15/630,909 Office Action dated Mar. 2, 2018.

Co-pending U.S. Appl. No. 16/056,310, filed Aug. 6, 2018.

Fineran, et al. Degenerate target sites mediate rapid primed CRISPR adaptation. Proc Natl Acad Sci U S A. Apr. 22, 2014;111(16):E1629-38. doi: 10.1073/pnas.1400071111. Epub Apr. 7, 2014.

Garst et al., (2017) 14 Supplementary Figures. Nature Biotechnology: doi:10.1038/nbt.3718.

Garst, et al., Genome-wide mapping of mutations at single-nucleotide resolution for protein, metabolic and genome engineering. Nature Biotechnology 35, 48-55 (2017) doi:10.1038/nbt.3718.

U.S. Appl. No. 15/116,616 Office Action dated Jul. 30, 2018.

U.S. Appl. No. 15/948,785 Office Action dated Jun. 4, 2018.

Bao, et al., Genome-scale engineering of *Saccharomyces cerevisiae* with single-nucleotide precision. Nature Biotechnology, May 7, 2018;36(6):505-508.

Richardson et al. Enhancing homology-directed genome editing by catalytically active and inactive CRISPR-Cas9 using asymmetric donor DNA. Nat Biotechnol 2016; 34(3):339-344.

Ronda, et al. CRMAGE: CRISPR Optimized MAGE Recombineering. Sci Rep. Jan. 22, 2016;6:19452. doi: 10.1038/srep19452.

Roy, et al., Multiplexed precision genome editing with trackable genomic barcodes in yeast. Nature Biotechnology, Jun. 2018; 36(6):512-524.

Sadhu, et al., Highly parallel genome variant engineering with CRISPR-Cas9. Nature genetics, Apr. 9, 2018; 50(4):510-514.

U.S. Appl. No. 15/116,616 Office Action dated Nov. 14, 2018.

U.S. Appl. No. 15/948,785 Office Action dated Nov. 2, 2018.

U.S. Appl. No. 16/056,310 Office Action dated Nov. 9, 2018.

Figure 2

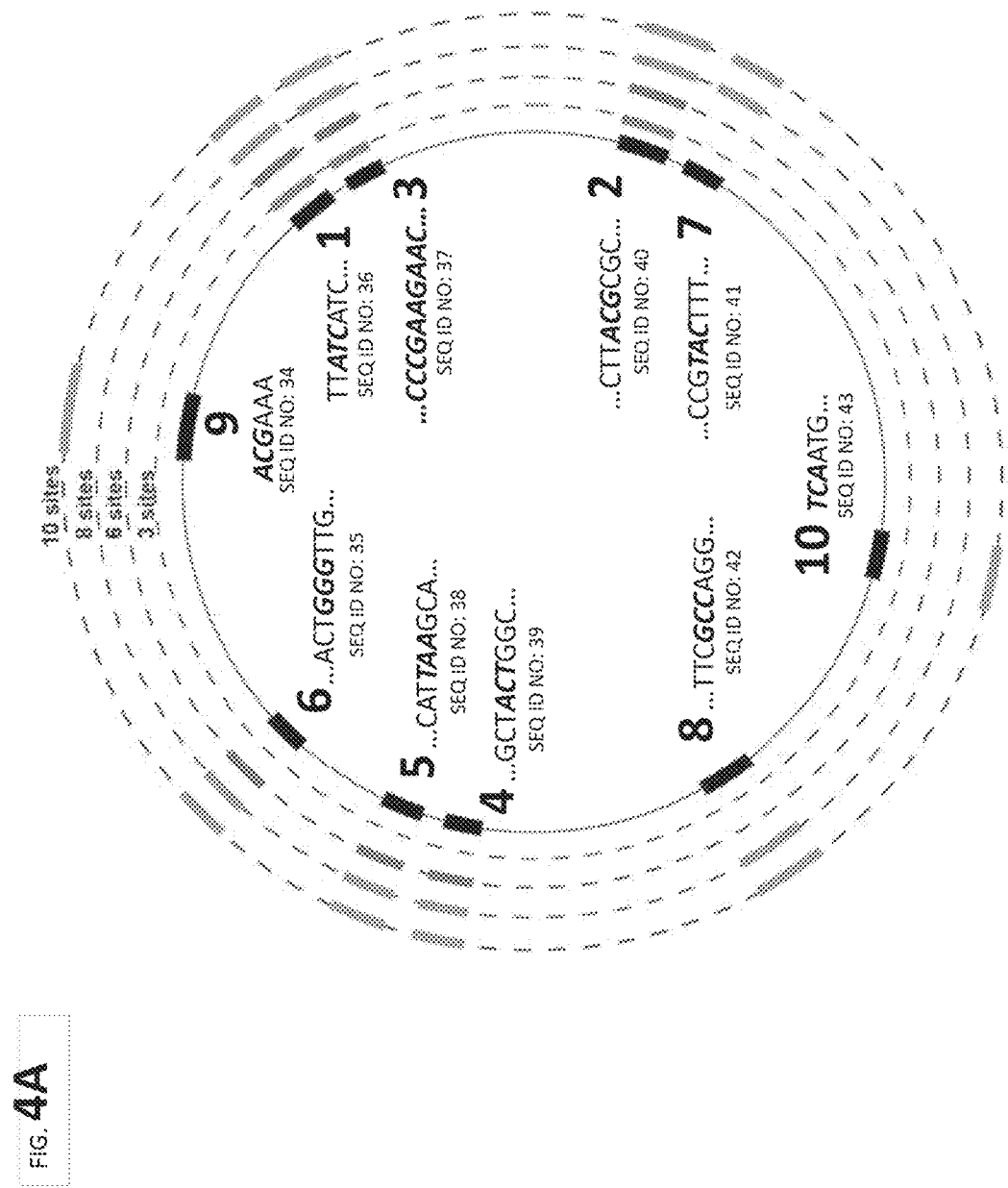

FIG. 4B

CGGAACCCGGTATTGCAGCAGCTTTATCATCGCGCTGGACGCGGCACAAATCGC
GCTTAACGGTCAGGAAGAACGGGCCATCGTGAATCCGCAACGCAATGACACT
CCGCCCAGCAGAACGGGGCGGTTGGTATGGTGTTTCAGTCTTACGGCTCTATCCCA
CCTGTCAGTAGCAGAAACATGCATTTGGCCTGAAACTGGCAAGCACGCGGGT
AGCAGAGCCCGAGTATTACATCGGATTTCAACAGCGGTAAGATCCTTGAG
AGTTTTGCGCGAGAAGTTTCTCAATGATGAGCACTTTAAAGTTGTGCTATG
TGGCGCGACGGTTCGGCGAGGATGTTCGGGACGTGAGCGTATGAAGAGCACTTT
GCGTTTGCGCTGCTACTGGCACACCTTCGTCTGGAACGGGGCGATATGTTT
TCAGATGGTTGCGAGTGGTGCACTTGACGCGGTTTATGATTGCAGGTCGCTGGGC
GGCTGGTGCATTAAGCACTTCGACCGCTGGGTAGACCAGATCAAACGCTAAGATCAAATGCCGAT
TGTCAGTTGGAGGGCGAAAGCCAATCACTCGGTCTGGATCGAACCAGAGCACTTCAAAAACTG
GGTTGAATGGGCGAAAGCCAATCACTCGGTCTGGATCGAACCATGCGTATCGTG
CCAAGTCGGTCCCAGACAACAAGTATTATCGGAGTTGTCGATCAACTCG
ATATACCGTTACTTTGTTATGGTTACGATTTCGAGTTGAATTATTATTGG
CAGCCCCCGTTGTGTGTCCTTCTGATGATCCCATTACACGGCCACGCTTGAGCCAG
GACCTGGCGGGCGAGAAATTCGCAGGATGGTCACTTACCGCACTACTTGCAA
CTTATCCGCTGTCCGAGGACGTTAACGCCACGAACCGCCACGAACCGCCACGACTTGTGATGAGTAGTAAAGCTG
CTACCATGACCGTTGCATAGGCATAATGACCGCCATAATGAATAGACATTTTGAG
GCATTTTCAGTCAGTTGCCCAATGTACCTATACCCAGACCGTCAGCTCAGATATTA

SEQ ID NO: 13

Experimental setup and proof of concept

CRISPR ENABLED MULTIPLEXED GENOME ENGINEERING

RELATED APPLICATION

This application is continuation application of U.S. patent application Ser. No. 15/630,909, filed Jun. 22, 2017, which is continuation application of U.S. patent application Ser. No. 15/116,616, filed Aug. 4, 2016, which is a national stage entry of International Application No. PCT/US2015/015476, filed Feb. 11, 2015, which claims the benefit under 35 U.S.C. § 119 of U.S. provisional application 61/938,608 filed Feb. 11, 2014, the entire teachings of each of which are incorporated herein by reference.

BACKGROUND OF THE INVENTION

Rational manipulation of large DNA constructs is a central challenge to current synthetic biology and genome engineering efforts. In recent years, a variety of technologies have been developed to address this challenge and increase the specificity and speed with which mutations can be generated. Additionally, adaptive mutations are a central driver of evolution, but their abundance and relative contribution to cellular phenotypes are poorly understood even in the most well-studied organisms. This can be attributed in large part to the technical challenges associated with observing and reconstructing these genotypes and correlating their presence with the phenotype of interest. For example, methods of genome editing that rely on random mutagenesis lead to complex genotypes consisting of many mutations, the relative contribution of each of which is difficult to deconvolute. Moreover, epistatic interactions between alleles are difficult to assign due to lack of information regarding the individual mutations.

SUMMARY OF THE INVENTION

Clustered Regularly Interspersed Short Palindromic Repeats (CRISPR) exist in many bacterial genomes and have been found to play an important role in adaptive bacterial immunity. Transcription of these arrays gives rise to CRISPR RNAs that direct sequence-specific binding of CRISPR/cas complexes to DNA targets in cells for gene repression or DNA cleavage. The specificity of these complexes allows novel in vivo applications for strain engineering.

Described herein are methods of rational, multiplexed manipulation of chromosomes within open reading frames (e.g., to generate protein libraries) or within multiple genes in any segment of a chromosome, in which various CRISPR systems are used. These methods provide more efficient combinatorial genome engineering than those previously available.

Expanding the multiplexing capabilities of CRISPR presents a current technological challenge and would enable use of these systems to generate rational libraries in high-throughput format. Such advances have broad reaching implications for the fields of metabolic and protein engineering that seek to refactor complex genetic networks for optimal production.

The methods comprise introducing components of the CRISPR system, including CRISPR-associated nuclease Cas9 and a sequence-specific guide RNA (gRNA) into cells, resulting in sequence-directed double stranded breaks using the ability of the CRISPR system to induce such breaks. Components of the CRISPR system, including the CRISPR-associated nuclease Cas9 and a sequence-specific guide RNA (gRNA), can be introduced into cells encoded on one or more vector, such as a plasmid. DNA recombineering cassettes or editing oligonucleotides can be rationally designed to include a desired mutation within a target locus and a mutation in a common location outside of the target locus that may be recognized by the CRISPR system. The described methods can be used for many applications, including altering a pathway of interest.

In one embodiment, the method is a method of genome engineering, comprising: (a) introducing into cells a vector that encodes: (i) an editing cassette that includes a region which is homologous to the target region of the nucleic acid in the cell and includes a mutation (referred to a desired mutation) of at least one nucleotide relative to the target region, such as a mutation of at least one nucleotide in at least one codon relative to the target region, and a protospacer adjacent motif (PAM) mutation; (ii) a promoter; and (iii) at least one guide RNA (gRNA), the gRNA comprising: (a) a region (RNA) complementary to a portion of the target region; and (b) a region (RNA) that recruits a Cas9 nuclease, thereby producing cells comprising the vector; (b) maintaining cells comprising the vector under conditions under which Cas9 is expressed, wherein Cas9 nuclease is encoded on the vector, encoded on a second vector or encoded on the genome of the cells, resulting in production of cells that comprise the vector and do not comprise the PAM mutation and cells that comprise the vector and the PAM mutation; (c) culturing the product of (b) under conditions appropriate for cell viability, thereby producing viable cells; (d) obtaining viable cells produced in (c); and (e) sequencing the editing oligonucleotide of the vector of at least one viable cell obtained in (d) and identifying the mutation of at least one codon.

In another embodiment, the method is a method of genome engineering by trackable CRISPR enriched recombineering, comprising: (a) introducing into a first population of cells a vector that encodes: (i) at least one editing cassette comprising: (a) a region homologous to a target region of a nucleic acid and comprising a mutation of at least one nucleotide relative to the target region, such as a mutation of at least one nucleotide in at least one codon relative to the target region, and (b) a protospacer adjacent motif (PAM) mutation; (ii) at least one promoter; and (iii) at least one guide RNA (gRNA) comprising: (a) a region (RNA) complementary to a portion of the target region and (b) a region (RNA) that recruits a Cas9 nuclease, thereby producing a second population of cells that comprise the vector; (b) maintaining the second population of cells under conditions in which Cas9 nuclease is expressed, wherein the Cas9 nuclease is encoded on the vector, a second vector or on the genome of cells of the second population of cells, resulting in DNA cleavage in cells that do not comprise the PAM mutation and death of such cells; (c) obtaining viable cells produced in (b); and (d) identifying the mutation of at least one codon by sequencing the editing oligonucleotide of the vector of at least one cell of the second population of cells.

Either of the above embodiments can further comprise synthesizing and/or obtaining a population of editing oligonucleotides. Either embodiment can further comprise amplifying the population of editing oligonucleotides. In any of the embodiments, the vector can further comprise a spacer, at least two priming sites or both a spacer and at least two priming sites. In some embodiments, the editing cassette comprises a target region comprising a mutation of at least one codon within 100 nucleotides of the PAM mutation.

Also described is a vector comprising:
(i) an editing cassette that includes a region which is homologous to a target region of a nucleic acid in a cell and includes a mutation (referred to a desired mutation) of at least one nucleotide relative to the target region, and a protospacer adjacent motif (PAM) mutation;
(ii) a promoter; and
(iii) at least one guide RNA (gRNA) comprising: (a) a region (RNA) complementary to a portion of the target region; and (b) a region (RNA) that recruits a Cas9 nuclease.

A further embodiment is a vector comprising:
(i) an editing cassette that includes a region which is homologous to a target region of a nucleic acid in a cell and includes a mutation (referred to a desired mutation) of at least one nucleotide in at least one codon relative to the target region, and a protospacer adjacent motif (PAM) mutation;
(ii) a promoter; and
(iii) at least one guide RNA (gRNA) comprising: (a) a region (RNA) complementary to a portion of the target region; and (b) a region (RNA) that recruits a Cas9 nuclease.

A further embodiment is a vector comprising:
(i) at least one editing cassette comprising: (a) a region homologous to a target region of a nucleic acid and comprising a mutation of at least one nucleotide relative to the target region and (b) a protospacer adjacent motif (PAM) mutation;
(ii) at least one promoter; and
(iii) at least one guide RNA (gRNA) comprising: (a) a region (RNA) complementary to a portion of the target region and (b) a region (RNA) that recruits a Cas9 nuclease.

Another embodiment of the vector is a vector comprising:
(i) at least one editing cassette comprising: (a) a region homologous to a target region of a nucleic acid and comprising a mutation of at least one nucleotide in at least one codon relative to the target region and (b) a protospacer adjacent motif (PAM) mutation;
(ii) at least one promoter; and
(iii) at least one guide RNA (gRNA) comprising: (a) a region (RNA) complementary to a portion of the target region and (b) a region (RNA) that recruits a Cas9 nuclease.

In any of the embodiments, the vector can further comprise a spacer; at least two priming sites; or a spacer and at least two priming sites. In those vectors in which the mutation is of at least one nucleotide in at least one codon, the editing cassette the mutation can be, for example, within 100 nucleotides of the PAM mutation.

Also described is a library comprising a population of cells produced by the methods described herein. A library of a population of cells can comprise cells having any of the vectors described herein. For example, a population of cells can comprise a vector that comprises:
(i) an editing cassette that includes a region which is homologous to a target region of a nucleic acid in a cell and includes a mutation (referred to a desired mutation) of at least one nucleotide relative to the target region, and a protospacer adjacent motif (PAM) mutation;
(ii) a promoter; and
(iii) at least one guide RNA (gRNA) comprising: (a) a region (RNA) complementary to a portion of the target region; and (b) a region (RNA) that recruits a Cas9 nuclease.

In a further embodiment, a population of cells can comprise a vector that comprises:
(i) an editing cassette that includes a region which is homologous to a target region of a nucleic acid in a cell and includes a mutation (referred to a desired mutation) of at least one nucleotide in at least one codon relative to the target region, and a protospacer adjacent motif (PAM) mutation;
(ii) a promoter; and
(iii) at least one guide RNA (gRNA) comprising: (a) a region (RNA) complementary to a portion of the target region; and (b) a region (RNA) that recruits a Cas9 nuclease.

In a further embodiment, the method is a method of CRISPR-assisted rational protein engineering (combinatorial genome engineering), comprising:
(a) constructing a donor library, which comprises recombinant DNA, such as recombinant chromosomes or recombinant DNA in plasmids, by introducing into, such as by co-transformation, a population of first cells (i) one or more editing oligonucleotides, such as rationally designed oligonucleotides, that couple deletion of a first single protospacer adjacent motif (PAM) with mutation of at least one codon in a gene adjacent to the PAM (the adjacent gene) and (b) a guide RNA (gRNA) that targets a nucleotide sequence 5' of the open reading frame of a chromosome, thereby producing a donor library that comprises a population of first cells comprising recombinant chromosomes having targeted codon mutations;
(b) amplifying the donor library constructed in (a), such as by PCR amplification, of recombinant chromosomes that uses a synthetic feature from the editing oligonucleotides and simultaneously incorporates a second PAM deletion (destination PAM deletion) at the 3' terminus of the gene, thereby coupling, such as covalently coupling, targeted codon mutations directly to the destination PAM deletion and producing a retrieved donor library carrying the destination PAM deletion and targeted codon mutations; and
(c) introducing (e.g., co-transforming) the donor library carrying the destination PAM deletion and targeted codon mutations and a destination gRNA plasmid into a population of second cells, which are typically a population of naïve cells, thereby producing a destination library comprising targeted codon mutations.

The population of first cells and the population of second cells (e.g., a population of naïve cells) are typically a population in which the cells are all of the same type and can be prokaryotes or eukaryotes, such as but not limited to bacteria, mammalian cells, plant cells, insect cells.

In some embodiments, the method further comprises maintaining the destination library under conditions under which protein is produced.

In some embodiments, the first cell expresses a polypeptide with Cas9 nuclease activity. In some embodiments, the polypeptide with Cas9 nuclease activity is expressed under control of an inducible promoter.

In some embodiments, the editing oligonucleotides are complementary to a (one, one or more, at least one) target nucleic acid present in the first cell. In some embodiments, the editing oligonucleotides target more than one target site or locus in the first cell. In some embodiments, the nucleic acid sequence of the editing oligonucleotides [desired codon] comprises one or more substitutions, deletions, insertions or any combination of substitutions, deletions and insertions relative to the target nucleic acid. In some embodiments, the editing oligonucleotides are rationally designed; in further embodiments, they are produced by random mutagenesis or by using degenerate primer oligonucleotides. In some embodiments, the editing oligonucleotides are derived from a collection of nucleic acids (library).

In some embodiments, the gRNA is encoded on a plasmid. In some embodiments, the editing oligonucleotide and the gRNA are introduced into the first cell by transformation, such as by co-transformation of the editing oligonucleotide and the guide (g) RNA. In some embodiments, the editing oligonucleotide and the gRNA are introduced sequentially into the first cell. In other embodiments, the editing oligonucleotide and the gRNA are introduced simultaneously into the first cell.

In some embodiments, retrieving the donor library further comprises (a) screening cells for incorporation of the editing oligonucleotide and (b) selecting cells that are confirmed to have incorporated the editing oligonucleotide. In some embodiments, retrieving the donor library further comprises processing of the retrieved donor library.

In some embodiments, the destination cell/naïve cell expresses a polypeptide with Cas9 nuclease activity. In some embodiments, the polypeptide with Cas9 nuclease activity is expressed under control of an inducible promoter.

Also described is a method of CRISPR-assisted rational protein engineering, comprising:
  (a) introducing (e.g., co-transforming) (i) synthetic dsDNA editing cassettes comprising editing oligonucleotides and (ii) a vector that expresses a guide RNA (gRNA) that targets genomic sequence just upstream of a gene of interest into a population of first cells, under conditions under which multiplexed recombineering and selective enrichment by gRNA of the editing oligonucleotides occur, thereby producing a donor library;
  (b) amplifying the donor library with an oligonucleotide that deletes a protospacer adjacent motif (PAM) adjacent to the 3' end of the gene of interest (destination PAM), thereby producing an amplified donor library comprising dsDNA editing cassettes from which the destination PAM has been deleted (with a 3' PAM deletion), rational codon mutations, and a P1 site;
  (c) processing the amplified donor library with an enzyme, such as a restriction enzyme (e.g., BsaI), to remove the P1 site; and
  (d) co-transforming a population of naïve cells with the amplified donor library processed in (c) and destination gRNA, thereby producing a population of co-transformed cells comprising dsDNA editing cassettes from which the destination PAM has been deleted (with a 3' PAM deletion), rational codon mutations and destination gRNA.

In all embodiments described, a mutation can be of any type desired, such as one or more insertions, deletions, substitutions or any combination of two or three of the foregoing (e.g., insertion and deletion; insertion and substitution; deletion and substitution; substitution and insertion; insertion, deletion and substitution). Insertions, deletions and substitutions can be of any number of nucleotides. They can be in codons (coding regions) and/or in noncoding regions.

BRIEF DESCRIPTION OF THE DRAWINGS

FIG. 1A shows a schematic of donor library construction. Synthetic dsDNA editing cassettes were co-transformed with a vector that expresses a guide RNA (gRNA) targeting the genomic sequence upstream of the gene of interest. The co-transformation generated a donor library via multiplexed recombineering of the editing oligonucleotides, which are selectively enriched by the gRNA. The donor library was then amplified using an oligonucleotide that mutates (deletes) a PAM adjacent to the 3' end of the gene (destination PAM). FIG. 1B shows a schematic of final protein library generation. The donor library was processed with BsaI to remove the P1 site, and the library of dsDNA cassettes with the 3'PAM deletion and rational codon mutations was co-transformed with the destination gRNA to generate the final protein library.

FIG. 2 presents the DNA sequence from clones from the galK donor library construction confirming incorporation of the P1 feature of the editing oligonucleotide at high efficiency as well as the mutation at the targeted codon position (underlined). The sequence of P1 is provided by SEQ ID NO: 1.

FIG. 4A presents linker and construct results. FIG. 4B shows 10 edits related to emulsion PCR based tracking.

FIG. 14A shows an overview of the design components. The GEn-TraCER cassettes contain guide RNA (gRNA) sequence(s) to target a specific site in the cell genome and cause dsDNA cleavage. A region of homology complementary to the target region mutates the PAM and other nearby desired sites. Cells that undergo recombination are selectively enriched to high abundance. Sequencing of the GEn-TraCER editing cassette in the vector enables tracking of the genomic edits/mutations. FIG. 14B shows an example editing cassette design for the E. coli galK gene at codon 145.

The PAM is deleted with the nearest available PAM mutation that can be made for synonymous change at the nearest available PAM position. This enables mutagenesis with a "silent scar" of 1-2 nucleotides at the PAM deletion site. FIG. 14C shows GEn-TraCER cassettes may be synthesized using array-based synthesis methods, thus enabling parallel synthesis of at least $10^4$-$10^6$ cassettes for systematic targeting and simultaneous evaluation of fitness for thousands of mutations on a genome-wide scale.

FIG. 16A shows the effect of the size of the editing cassette on efficiency of the method. FIG. 16B shows the effect of the distance between the PAM mutation/deletion and the desired mutation on efficiency of the method.

FIG. 16C shows the effect of the presence or absence of the MutS system on efficiency of the method.

DETAILED DESCRIPTION OF THE INVENTION

Bacterial and archaeal CRISPR systems have emerged as powerful new tools for precision genome editing. The type-II CRISPR system from *Streptococcus pyogenes* (*S. pyogenes*) has been particularly well characterized in vitro, and simple design rules have been established for reprogramming its double-stranded DNA (dsDNA) binding activity (Jinek et al. *Science* (2012) 337(6096): 816-821). Use of CRISPR-mediated genome editing methods has rapidly accumulated in the literature in a wide variety of organisms, including bacteria (Cong et al. *Science* (2013) 339 (6121): 819-823), *Saccharomyces cerevisiae* (DiCarlo et al. *Nucleic Acids Res.* (2013) 41:4336-4343), *Caenorhabditis elegans* (Waaijers et al. *Genetics* (2013) 195: 1187-1191) and various mammalian cell lines (Cong et al. *Science* (2013) 339 (6121): 819-823; Wang et al. *Cell* (2013) 153:910-918). Like other endonuclease based genome editing technologies, such as zinc-finger nucleases (ZFNs), homing nucleases and TALENS, the ability of CRISPR systems to mediate precise genome editing stems from the highly specific nature of target recognition. For example, the type-I CRISPR system from *Escherichia coli* and the *S. pyogenes* system require perfect complementarity between the CRISPR RNA (crRNA) and a 14-15 base pair recognition target, suggesting that the immune functions of CRISPR systems are naturally employed (Jinek et al. *Science* (2012) 337(6096): 816-821; Brouns et al. *Science* (2008) 321:960-964; Semenova et al. *PNAS* (2011) 108:10098-10103).

Described herein are methods for genome editing that employ an endonuclease, such as the Cas9 nuclease encoded by a cas9 gene, to perform directed genome evolution/produce changes (deletions, substitutions, additions) in DNA, such as genomic DNA. The cas9 gene can be obtained from any source, such as from a bacterium, such as the bacterium *S. pyogenes*. The nucleic acid sequence of the cas9 and/or amino acid sequence of Cas9 may be mutated, relative to the sequence of a naturally occurring cas9 and/or Cas9; mutations can be, for example, one or more insertions, deletions, substitutions or any combination of two or three of the foregoing. In such embodiments, the resulting mutated Cas9 may have enhanced or reduced nuclease activity relative to the naturally occurring Cas9.

Figure 1B:
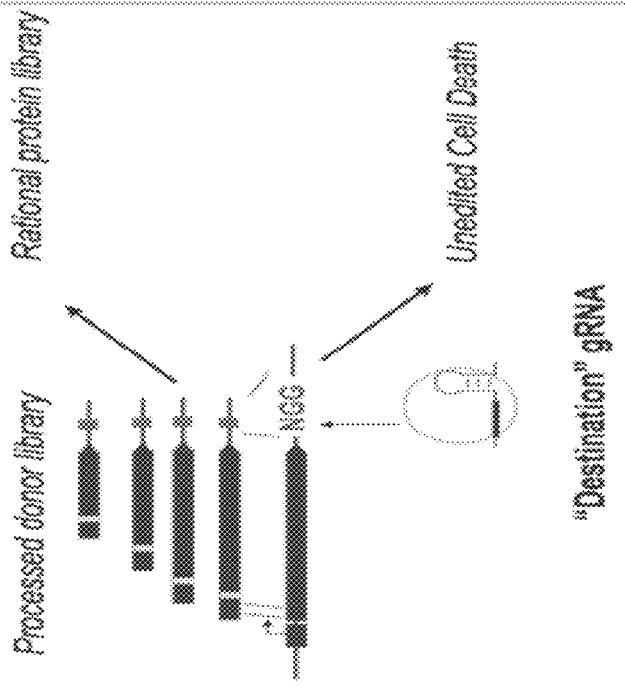
FIGS. 1A and 1B present an overview of CRISPR assisted rational protein engineering (CARPE).
Figure 1A:
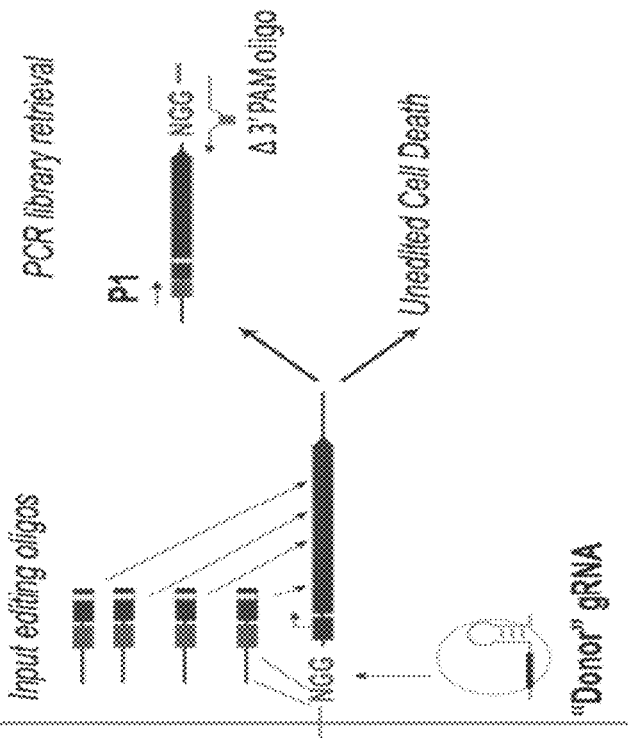
Figure 11A:
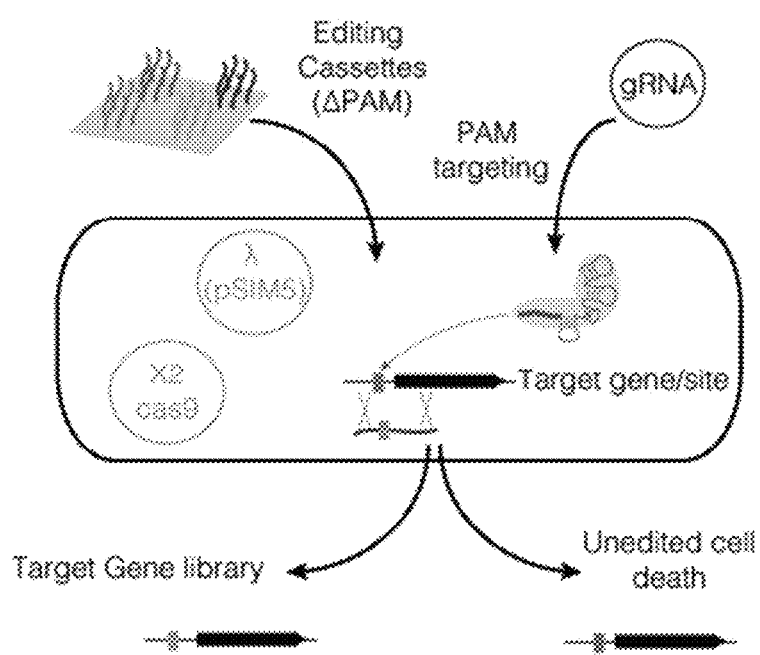
FIG. 11A shows a schematic of multiplex CRISPR-based editing using CARPE.

FIGS. 1A, 1B, and 11A present a CRISPR-mediate genome editing method referred to as CRISPR Assisted Rational Protein Engineering (CARPE). CARPE is a two stage construction process which relies on generation of "donor" and "destination" libraries that incorporate directed mutations from single-stranded DNA (ssDNA) or double-stranded DNA (dsDNA) editing cassettes directly into the genome. In the first stage of donor construction (FIG. 1A), rationally designed editing oligos are cotransformed into cells with a guide RNA (gRNA) that hybridizes to/targets a target DNA sequence, such as a sequence 5' of an open reading frame or other sequence of interest. A key innovation of CARPE is in the design of the editing oligonucleotides that couple deletion or mutation of a single protospacer adjacent motif (PAM) with the mutation of one or more desired codons in the adjacent gene, thereby enabling generation of the entire donor library in a single transformation. The donor library is then retrieved by amplification of the recombinant chromosomes, e.g. by a PCR reaction, using a synthetic feature from the editing oligonucleotide; a second PAM deletion or mutation is simultaneously incorporated at the 3' terminus of the gene. This approach thus covalently couples the codon targeted mutations directly to a PAM deletion. In the second stage of CARPE (FIG. 1B) the PCR amplified donor libraries carrying the destination PAM deletion/mutation and the targeted mutations (desired mutation(s) of one or more nucleotides, such as one or more nucleotides in one or more codons) are co-transformed into naïve cells with a destination gRNA vector to generate a population of cells that express a rationally designed protein library.

In the CRISPR system, the CRISPR trans-activating (tracrRNA) and the spacer RNA (crRNA) guide selection of a target region. As used herein, a target region refers to any locus in the nucleic acid of a cell or population of cells in which a mutation of at least one nucleotide, such as a mutation of at least one nucleotide in at least one codon (one or more codons), is desired. The target region can be, for example, a genomic locus (target genomic sequence) or extrachromosomal locus. The tracrRNA and crRNA can be expressed as a single, chimeric RNA molecule, referred to as a single-guide RNA, guide RNA, or gRNA. The nucleic acid sequence of the gRNA comprises a first nucleic acid sequence, also referred to as a first region, that is complementary to a region of the target region and a second nucleic acid sequence, also referred to a second region, that forms a stem loop structure and functions to recruit Cas9 to the target region. In some embodiments, the first region of the gRNA is complementary to a region upstream of the target genomic sequence. In some embodiments, the first region of the gRNA is complementary to at least a portion of the target region. The first region of the gRNA can be completely complementary (100% complementary) to the target genomic sequence or include one or more mismatches, provided that it is sufficiently complementary to the target genomic sequence to specifically hybridize/guide and recruit Cas9. In some embodiments, the first region of the gRNA is at least 15, 16, 17, 18, 19, 20, 21, 22, 23, 24, 25, 26, 27, 28, 29, or at least 30 nucleotides in length. In some embodiments, the first region of the gRNA is at least 20 nucleotides in length. In some embodiments the stem loop structure that is formed by the second nucleic acid sequence is at least 50, 51, 52, 53, 54, 55, 56, 57, 58, 59, 60, 61, 62, 63, 64, 65, 66, 67, 68, 69, 70, 7, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides in length. In specific embodiments, the stem loop structure is from 80 to 90 or 82 to 85 nucleotides in length and, in further specific embodiments, the second region of the gRNA that forms a stem loop structure is 83 nucleotides in length.

In some embodiments, the sequence of the gRNA (of the donor library) that is introduced into the first cell using the CARPE method is the same as the sequence of the gRNA (of the destination library) that is introduced into the second/naïve cell. In some embodiments, more than one gRNA is introduced into the population of first cells and/or the population of second cells. In some embodiments, the more than one gRNA molecules comprise first nucleic acid sequences that are complementary to more than one target region.

In the CARPE method, double stranded DNA cassettes, also referred to as editing oligonucleotides, for use in the described methods can be obtained or derived from many sources. For example, in some embodiments, the dsDNA cassettes are derived from a nucleic acid library that has been diversified by nonhomologous random recombination (NRR); such a library is referred to as an NRR library. In some embodiments, the editing oligonucleotides are synthesized, for example by array-based synthesis. The length of the editing oligonucleotide may be dependent on the method used in obtaining the editing oligonucleotide. In some embodiments, the editing oligonucleotide is approximately 50-200 nucleotides, 75-150 nucleotides, or between 80-120 nucleotides in length.

An editing oligonucleotide includes (a) a region that is homologous to a target region of the nucleic acid of the cell and includes a mutation (referred to a desired mutation) of at least one codon relative to the target region, and (b) a protospacer adjacent motif (PAM) mutation. The PAM mutation may be any insertion, deletion or substitution of one or more nucleotides that mutates the sequence of the PAM such that it is no longer recognized by the CRISPR system. A cell that comprises such a PAM mutation may be said to be "immune" to CRISPR-mediated killing. The desired mutation relative to the sequence of the target region may be an insertion, deletion, and/or substitution of one or more nucleotides at at least one codon of the target region.

The CARPE method is described below with reference to a bacterial gene for purposes of illustration only. The methods may be applied to any gene(s) of interest, including genes from any prokaryote including bacteria and archaea, or any eukaryote, including yeast and mammalian (including human) genes. The CARPE method was carried out on the galK gene in the *E. coli* genome, in part due to the availability of activity assays for this gene. The method was carried out using BW23115 parental strains and the pSIM5 vector (Datta et al. *Gene* (2008) 379:109-115) to mediate recombineering. The cas9 gene was cloned into the pBTBX-2 backbone under the control of a pBAD promoter to allow control of the cleavage activity by addition of arabinose. Assessment of the ability to selectively incorporate synthetic dsDNA cassettes (127 bp) was carried out using dsDNA cassettes from NNK libraries that were constructed from degenerate primers and/or from rationally designed oligonucleotides (oligos) synthesized as part of a 27,000 member library via microarray technology. In both cases, the oligonucleotides were designed to mutate the active site residues of the galK gene product. Highly efficient recovery of donor strain libraries was verified based on changes in the amplicon sizes obtained with primers directed at the galK locus. Sequencing of these colony PCR products from the NRR libraries indicated that the synthetic priming site (P1) from the dsDNA cassettes was incorporated with about 90-100% efficiency. This indicated that these libraries can be generated with high efficiency without reliance on the error prone mutS knockout strains that have typically been used in other recombineering based editing approaches (Costantino et al. *PNAS* (2003) 100:15748-15753; Wang et al. *Nature* (2009) 460:894-898). There was a drop in the efficiency of the codon mutations (about 20%), which may be due to mutS corrections during allelic replacement. Preliminary assessment of clones in the destination libraries indicated that the final codon editing efficiency was about 10% when both phases of construction are carried out in the mutS$^+$ background.

Comparison with other recently-published protocols for co-selectable editing was done, using alternative protocols that do not covalently link the PAM and codon mutations, but instead rely on their proximity to one another during replication (Wang et al. *Nat. Methods* (2012) 9:591-593). In these non-covalent experiments the same editing oligos as above were used and efforts were made to co-select for their insertion using the ssDNA oligos that target the same donor/destination PAM sites. Colony screening of the resultant mutants reveals high efficiency in recovery of the PAM mutants. However, there does not appear to be a strong co-selection for insertion of dsDNA editing cassettes. This may be due to large differences in the relative recombineering efficiencies of the PAM deletion oligonucleotides and the editing cassettes which generate sizable chromosomal deletions.

The ability to improve final editing efficiencies of the CARPE method can be assessed, such as by carrying out donor construction in mutS deficient strains before transferring to a wild-type donor strain in an effort to prevent loss of mutations during the donor construction phase. In addition, the generality of the CARPE method can be assessed, such as by utilizing CARPE on a number of essential genes, including dxs, metA, and folA. Essential genes have been effectively targeted using gRNA design strategies described. Results also indicate that despite the gene disruption that occurs during the donor library creation, the donor libraries can be effectively constructed and retrieved within 1-3 hours post recombineering.

Also provided herein are methods for trackable, precision genome editing using a CRISPR-mediated system referred to as Genome Engineering by Trackable CRISPR Enriched Recombineering (GEn-TraCER). The GEn-TraCER methods achieve high efficiency editing/mutating using a single vector that encodes both the editing cassette and gRNA. When used with parallel DNA synthesis, such as array-based DNA synthesis, GEN-TraCER provides single step generation of thousands of precision edits/mutations and makes it possible to map the mutation by sequencing the editing cassette on the vector, rather than by sequencing of the genome of the cell (genomic DNA). The methods have broad utility in protein and genome engineering applications, as well as for reconstruction of mutations, such as mutations identified in laboratory evolution experiments.

Figure 11B:
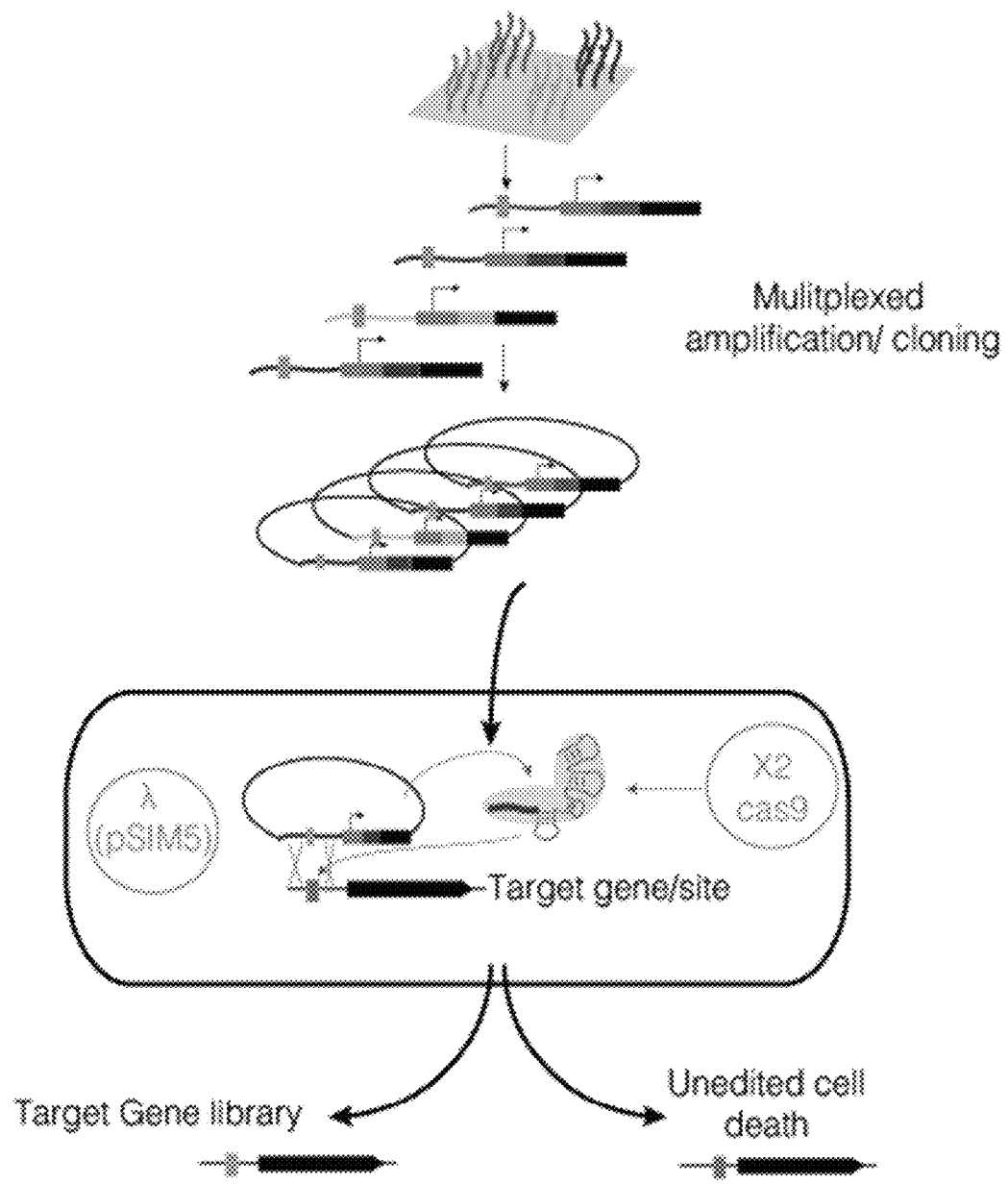
FIG. 11B shows a schematic of multiplex CRISPR-based editing using genome engineering by trackable CRISPR enriched recombineering (GEn-TraCER).

The GEn-TraCER methods and vectors combine an editing cassette, which includes a desired mutation and a PAM mutation, with a gene encoding a gRNA on a single vector, which makes it possible to generate a library of mutations in a single reaction. As shown in FIG. 11B, the method involves introducing a vector comprising an editing cassette that includes the desired mutation and the PAM mutation into a cell or population of cells. In some embodiments, the cells into which the vector is introduced also encodes Cas9. In some embodiments, a gene encoding Cas9 is subsequently introduced into the cell or population of cells. Expression of the CRISPR system, including Cas9 and the gRNA, in the cell or cell population is activated; the gRNA recruits Cas9 to the target region, where dsDNA cleavage occurs. Without wishing to be bound by any particular theory, the homologous region of the editing cassette complementary to the target region mutates the PAM and the one or more codon of the target region. Cells of the population of cells that did not integrate the PAM mutation undergo unedited cell death due to Cas9-mediated dsDNA cleavage. Cells of the population of cells that integrate the PAM mutation do not undergo cell death; they remain viable and are selectively enriched to high abundance. Viable cells are obtained and provide a library of targeted mutations.

The method of trackable genome editing using GEn-TraCER comprises: (a) introducing a vector that encodes at least one editing cassette, a promoter, and at least one gRNA into a cell or population of cells, thereby producing a cell or population of cells comprising the vector (a second population of cells); (b) maintaining the second population of cells under conditions in which Cas9 is expressed, wherein the Cas9 nuclease is encoded on the vector, a second vector or on the genome of cells of the second population of cells, resulting in DNA cleavage and death of cells of the second population of cells that do not comprise the PAM mutation, whereas cells of the second population of cells that comprise the PAM mutation are viable; (c) obtaining viable cells; and (d) sequencing the editing cassette of the vector in at least one cell of the second population of cells to identify the mutation of at least one codon.

In some embodiments, a separate vector encoding cas9 is also introduced into the cell or population of cells. Introducing a vector into a cell or population of cells can be performed using any method or technique known in the art. For example, vectors can be introduced by standard protocols, such as transformation including chemical transformation and electroporation, transduction and particle bombardment.

An editing cassette includes (a) a region, which recognizes (hybridizes to) a target region of a nucleic acid in a cell or population of cells, is homologous to the target region of the nucleic acid of the cell and includes a mutation (referred to a desired mutation) of at least one nucleotide in at least one codon relative to the target region, and (b) a protospacer adjacent motif (PAM) mutation. The PAM mutation may be any insertion, deletion or substitution of one or more nucleotides that mutates the sequence of the PAM such that the mutated PAM (PAM mutation) is not recognized by the CRISPR system. A cell that comprises such as a PAM mutation may be said to be "immune" to CRISPR-mediated killing. The desired mutation relative to the sequence of the target region may be an insertion, deletion, and/or substitution of one or more nucleotides at at least one codon of the target region. In some embodiments, the distance between the PAM mutation and the desired mutation is at least 5, 6, 7, 8, 9, 10, 11, 12, 13, 14, 15, 16, 17, 18, 19, 20, 21, 22, 23, 24, 25, 26, 27, 28, 29, 30 nucleotides on the editing cassette. In some embodiments, the PAM mutation is located at least 9 nucleotides from the end of the editing cassette. In some embodiments, the desired mutation is located at least 9 nucleotides from the end of the editing cassette.

In some embodiments, the desired mutation relative to the sequence of the target region is an insertion of a nucleic acid sequence. The nucleic acid sequence inserted into the target region may be of any length. In some embodiments, the nucleic acid sequence inserted is at least 50, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, or at least 2000 nucleotides in length. In embodiments in which a nucleic acid sequence is inserted into the target region, the editing cassette comprises a region that is at least 30, 31, 32, 33, 34, 35, 36, 37, 38, 39, 40, 41, 42, 43, 44, 45, 46, 47, 48, 49, 50 51, 52, 53, 54, 55, 56, 57, 58, 59, or at least 60 nucleotides in length and homologous to the target region.

The term "GEn-TraCER cassette" may be used to refer to an editing cassette, promoter, spacer sequence and at least a portion of a gene encoding a gRNA. In some embodiments, portion of the gene encoding the gRNA on the GEn-TraCER cassette encodes the portion of the gRNA that is complementary to the target region. In some embodiments, the portion of the gRNA that is complementary to the target region is at least 15, 16, 17, 18, 19, 20, 21, 22, 23, 24, 25, 26, 27, 28, 29, or at least 30 nucleotides in length. In some embodiments, the portion of the gRNA that is complementary to the target region is 24 nucleotides in length. In some embodiments, the GEn-TraCER cassette further comprising at least two priming sites. In some embodiments, the priming sites may be used to amplify the GEn-TraCER cassette, for example by PCR. In some embodiments, the portion of the gRNA is that complementary to the target region is used as a priming site.

In the GEn-TraCER method, editing cassettes and GEn-TraCER cassettes for use in the described methods can be obtained or derived from many sources. For example, in some embodiments, the editing cassette is synthesized, for example by array-based synthesis. In some embodiments, the GEn-TraCER cassette is synthesized, for example by array-based synthesis. The length of the editing cassette and/or GEn-TraCER cassette may be dependent on the method used in obtaining the editing cassette and/or the GEn-TraCER cassette. In some embodiments, the editing cassette is approximately 50-300 nucleotides, 75-200 nucleotides, or between 80-120 nucleotides in length. In some embodiments, the GEn-TraCER cassette is approximately 50-300 nucleotides, 75-200 nucleotides, or between 80-120 nucleotides in length.

In some embodiments, the method also involves obtaining GEn-TraCER cassettes, for example by array-based synthesis, and constructing the vector. Methods of constructing a vector will be known to one ordinary skill in the art and may involve ligating the GEn-TraCER cassette into a vector. In some embodiments, the GEn-TraCER cassettes or a subset (pool) of the GEn-TraCER cassettes are amplified prior to construction of the vector, for example by PCR.

The cell or population of cells comprising the vector and also encoding Cas9 are maintained or cultured under conditions in which Cas9 is expressed. Cas9 expression can be controlled. The methods described herein involve maintaining cells under conditions in which Cas9 expression is activated, resulting in production of Cas9. Specific conditions under which Cas9 is expressed will depend on factors, such as the nature of the promoter used to regulate Cas9 expression. In some embodiments, Cas9 expression is induced in the presence of an inducer molecule, such as arabinose. When the cell or population of cells comprising Cas9-encoding DNA are in the presence of the inducer molecule, expression of Cas9 occurs. In some embodiments, Cas9 expression is repressed in the presence of a repressor molecule. When the cell or population of cells comprising Cas9-encoding DNA are in the absence of a molecule that represses expression of Cas9, expression of Cas9 occurs.

Cells of the population of cells that remain viable are obtained or separated from the cells that undergo unedited cell death as a result of Cas9-mediated killing; this can be done, for example, by spreading the population of cells on culture surface, allowing growth of the viable cells, which are then available for assessment.

The desired mutation coupled to the PAM mutation is trackable using the GEn-TraCER method by sequencing the editing cassette on the vector in viable cells (cells that integrate the PAM mutation) of the population. This allows for facile identification of the mutation without the need to sequence the genome of the cell. The methods involve sequencing of the editing cassette to identify the mutation of one of more codon. Sequencing can be performed of the editing cassette as a component of the vector or after its separation from the vector and, optionally, amplification. Sequencing may be performed using any sequencing method known in the art, such as by Sanger sequencing.

The methods described herein can be carried out in any type of cell in which the CRISPR system can function (e.g., target and cleave DNA), including prokaryotic and eukaryotic cells. In some embodiments the cell is a bacterial cell, such as *Escherichia* spp. (e.g., *E. coli*). In other embodiments, the cell is a fungal cell, such as a yeast cell, e.g., *Saccharomyces* spp. In other embodiments, the cell is an algal cell, a plant cell, an insect cell, or a mammalian cell, including a human cell.

A "vector" is any of a variety of nucleic acids that comprise a desired sequence or sequences to be delivered to or expressed in a cell. The desired sequence(s) can be included in a vector, such as by restriction and ligation or by recombination. Vectors are typically composed of DNA, although RNA vectors are also available. Vectors include, but are not limited to: plasmids, fosmids, phagemids, virus genomes and artificial chromosomes.

Vectors useful in the GEN-TraCER method comprise at least one editing cassette as described herein, a promoter, and at least one gene encoding a gRNA. In some embodiments more than one editing cassette (for example 2, 3, 4, 5, 6, 7, 8, 9, 10 or more editing cassettes) are included on the vector. In some embodiments, the more than one editing cassettes are homologous with different target regions (e.g., there are different editing cassettes, each of which is homologous with a different target region). Alternatively or in addition, the vector may include more than one gene encoding more than one gRNA, (e.g., 2, 3, 4, 5, 6, 7, 8, 9, 10 or more gRNAs). In some embodiments, the more than one gRNAs contain regions that are complementary to a portion of different target regions (e.g., there are different gRNAs, each of which is complementary to a portion of a different target region).

In some embodiments, a GEn-TraCER cassette comprising at least one editing cassette, a promoter and a gene encoding a portion of a gRNA are ligated into a vector that encodes another portion of a gRNA. Upon ligation, the portion of the gRNA from the GEn-TraCER cassette and the other portion of the gRNA are ligated and form a functional gRNA.

The promoter and the gene encoding the gRNA are operably linked. In some embodiments, the methods involve introduction of a second vector encoding Cas9. In such embodiments, the vector may further comprise one or more promoters operably linked to a gene encoding Cas9. As used herein, "operably" linked means the promoter affects or regulates transcription of the DNA encoding a gene, such as the gene encoding the gRNA or the gene encoding Cas9. The promoter can be a native promoter (a promoter present in the cell into which the vector is introduced). In some embodiments, the promoter is an inducible or repressible promoter (the promoter is regulated allowing for inducible or repressible transcription of a gene, such as the gene encoding the gRNA or the gene encoding Cas9), such as promoters that are regulated by the presence or absence of a molecule (e.g., an inducer or a repressor). The nature of the promoter needed for expression of the gRNA may vary based on the species or cell type and will be recognized by one of ordinary skill in the art.

In some embodiments, the method comprises introducing a separate vector encoding Cas9 into the cell or population of cells before or at the same time as introduction of the vector comprising at least one editing cassette as described herein, a promoter and at least one gRNA. In some embodiments, the gene encoding Cas9 is integrated into the genome of the cell or population of cells. The Cas9-encoding DNA can be integrated into the cellular genome before introduction of the vector comprising at least one editing cassette as described herein, a promoter, and at least one gRNA or after introduction of the vector comprising at least one editing cassette as described herein, a promoter, and at least one gRNA. Alternatively, a nucleic acid molecule, such as DNA-encoding Cas9, can be expressed from DNA integrated into the genome. In some embodiments, the gene encoding Cas9 is integrated into the genome of the cell.

Vectors useful in the GEn-TraCER methods described herein may further comprise a spacer sequence, two or more priming sites or both a spacer sequence and two or more priming sites. In some embodiments, the presence of priming sites flanking the GEn-TraCER cassette allows amplification of the editing cassette, promoter and gRNA nucleic acid sequences.

EXAMPLES

Example 1: Using the CARPE Method to Edit galK

The CARPE approach was-carried out on the galactokinase gene, galK, in the *E. coli* genome; there are many available assays to assess the activity of the gene product. The experiments were carried out using *E. coli* BW23115 parental strain and the pSIM5 vector (Datta et al. *Gene* (2008) 379:109-115) to mediate recombineering. The gene encoding Cas9 was cloned into the pBTBX-2 backbone under the control of a pBAD promoter to allow control of the Cas9 cleavage activity by addition of arabinose to the culture medium.

Figure 2:
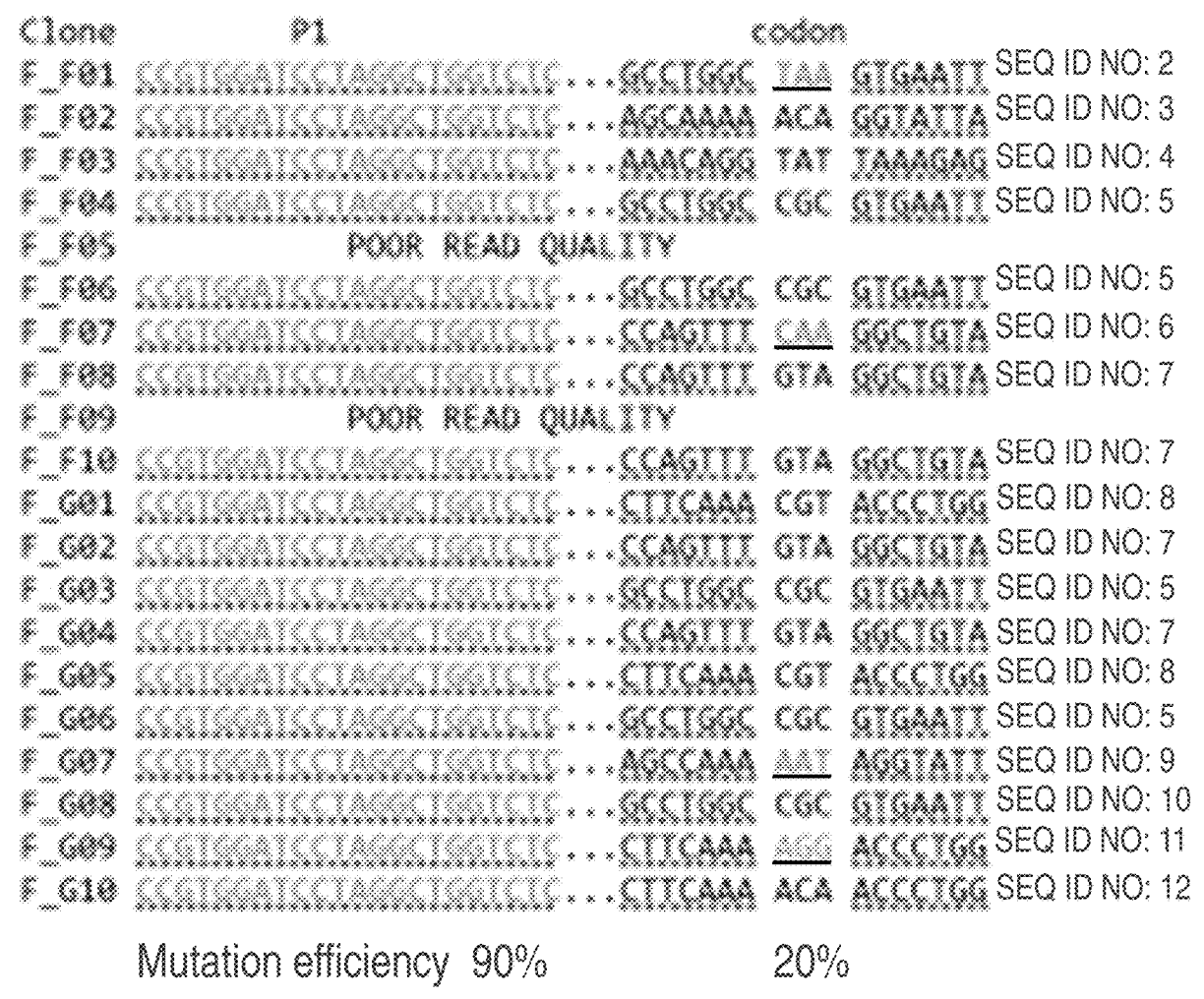

First, the ability to selectively incorporate of synthetic dsDNA cassettes (127 bp) was tested. The synthetic dsDNA cassettes were derived from NNR libraries that were constructed from degenerate primers or from rationally designed oligos synthesized as part of a 27,000 member library via microarray technology. In both cases, the oligonucleotides were designed to mutate the active site residues of the galK gene product as well as contain the synthetic priming site, P1 (SEQ ID NO: 1). Highly efficient recovery of donor strain libraries was verified based on changes in the amplicon sizes obtained by colony PCR using primers directed at the galK locus. Sequencing of the colony PCR products from the NNR libraries indicated that the synthetic priming site (P1) from the dsDNA cassettes was incorporated with about 90-100% efficiency (FIG. 2). This surprising and unexpected result suggests that libraries can be generated with high efficiency without reliance on the error prone mutS-deficient strains that have typically been used in other recombineering-based editing approaches (Constantino, et al. *PNAS* (2003) 100:15748-15753; Wang et al. *Nature* (2009) 460: 894-898). However, there was a drop in the efficiency of the codon mutations (about 20%), which may be due to correction by MutS during allelic replacement. In this work, the final codon editing efficiency was about 10% when both phases of construction were carried out in the mutS+ background.

To enhance the final editing efficiencies and generality of the CARPE method, the donor construction may be performed in mutS-deficient strains before transferring to a mutS+ donor strain in an effort to prevent loss of mutations during the donor construction phase.

Example 2: Using the CARPE Method to Target Essential Genes

Figure 3A:
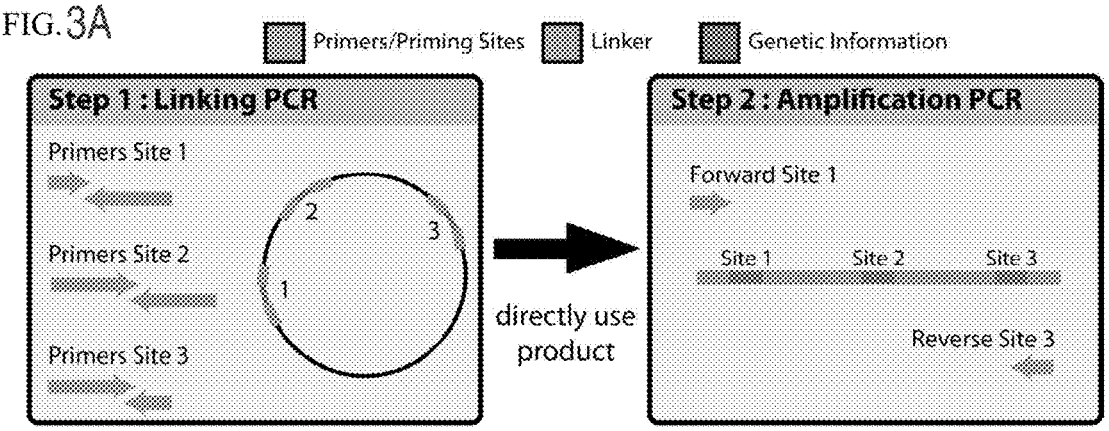
FIG. 3A shows primer design.
Figure 3B:
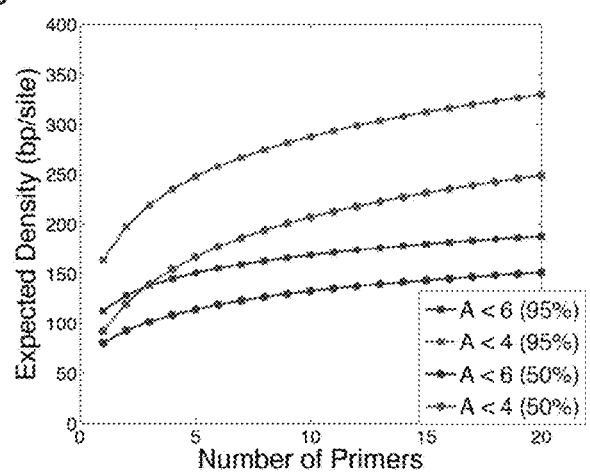
FIG. 3B shows the expected density relative to the number primers.
Figure 5:
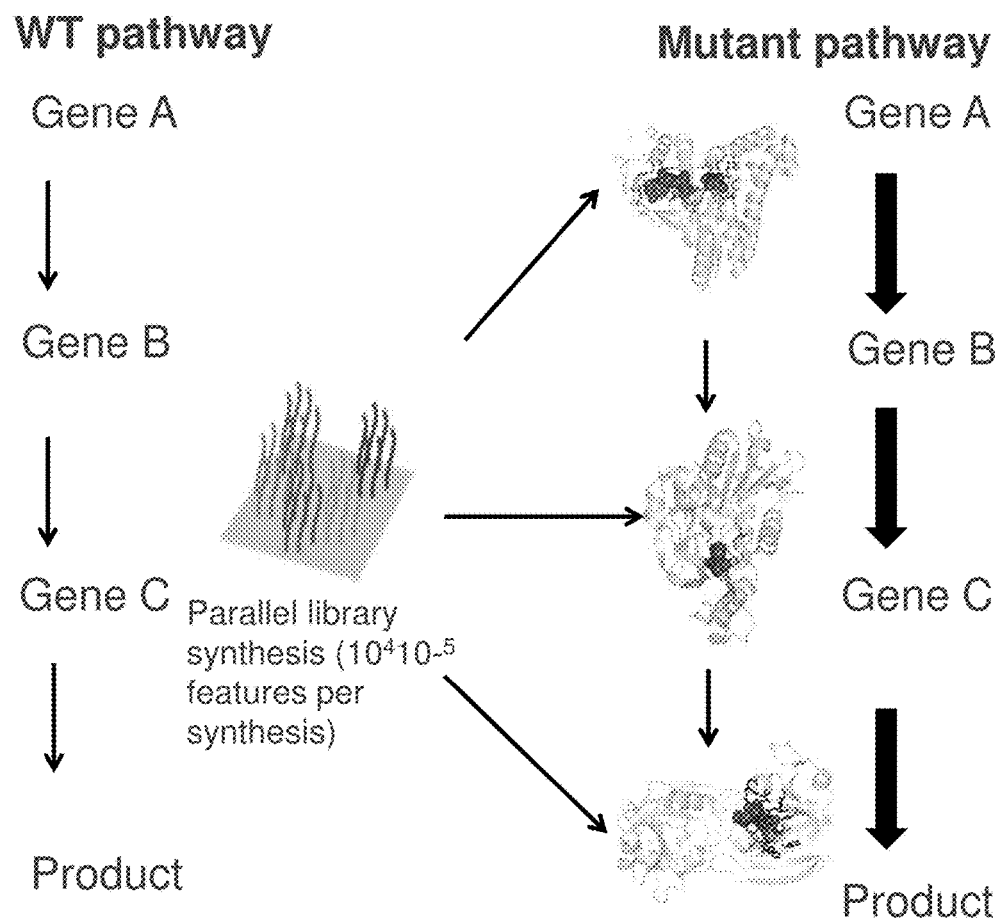
FIG. 5 is a schematic of rational protein editing for metabolic engineering.
Figure 6:
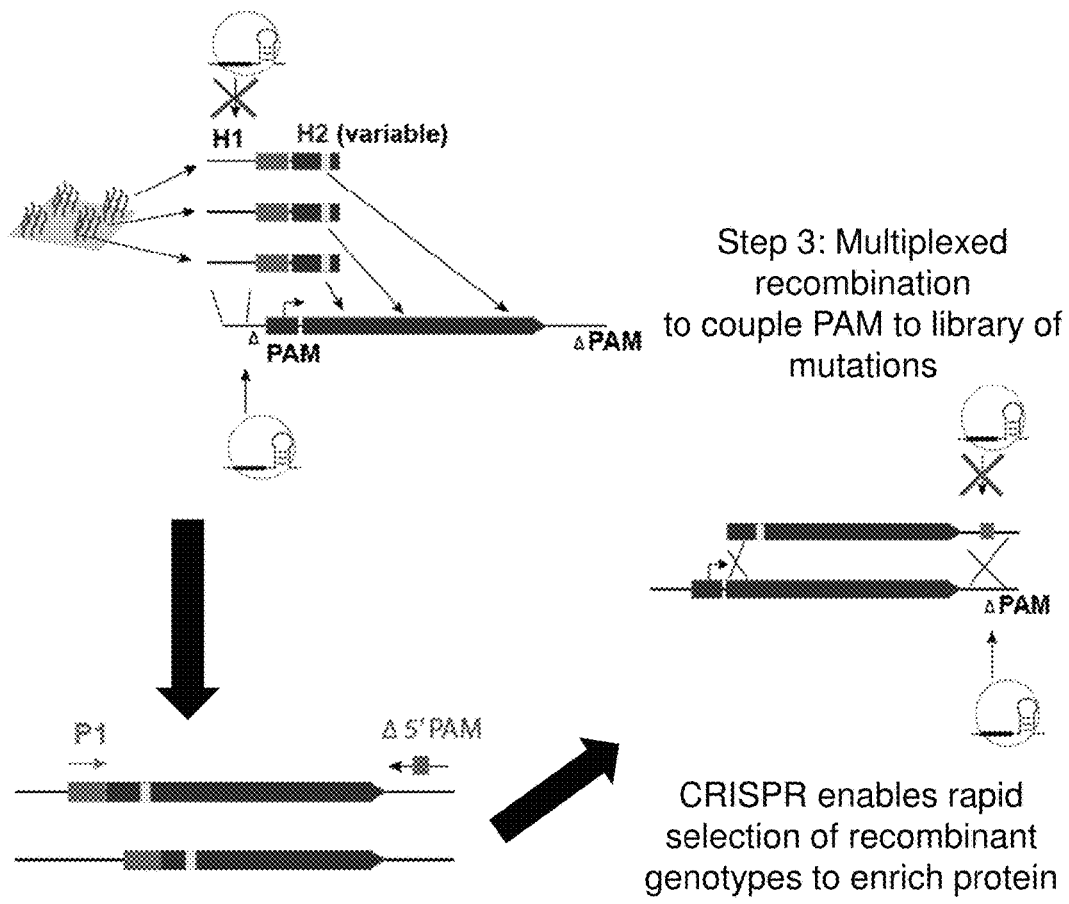
FIG. 6 is a schematic of the generation of CRISPR enriched rational protein libraries.
Figure 7:
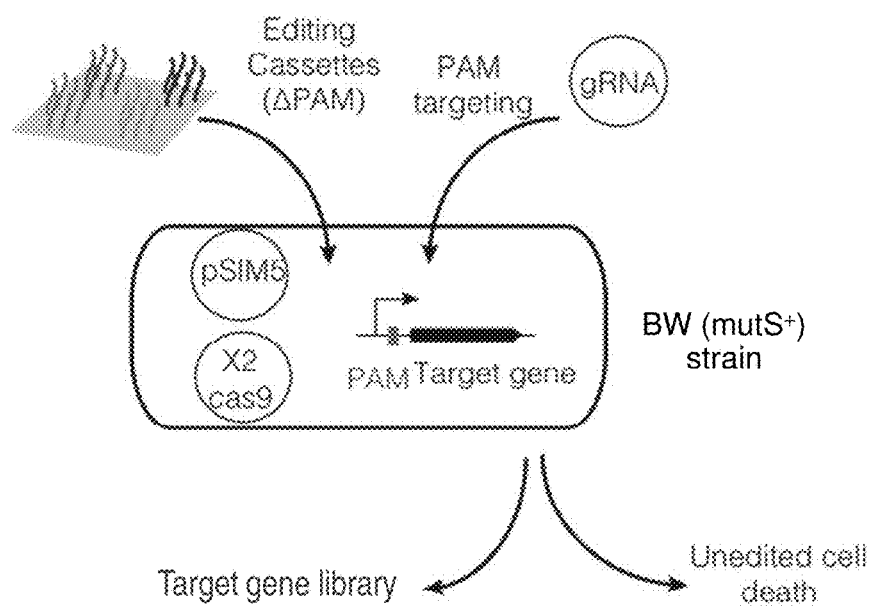
FIG. 7 is a schematic of setup and demonstration of CARPE.
Figure 8:
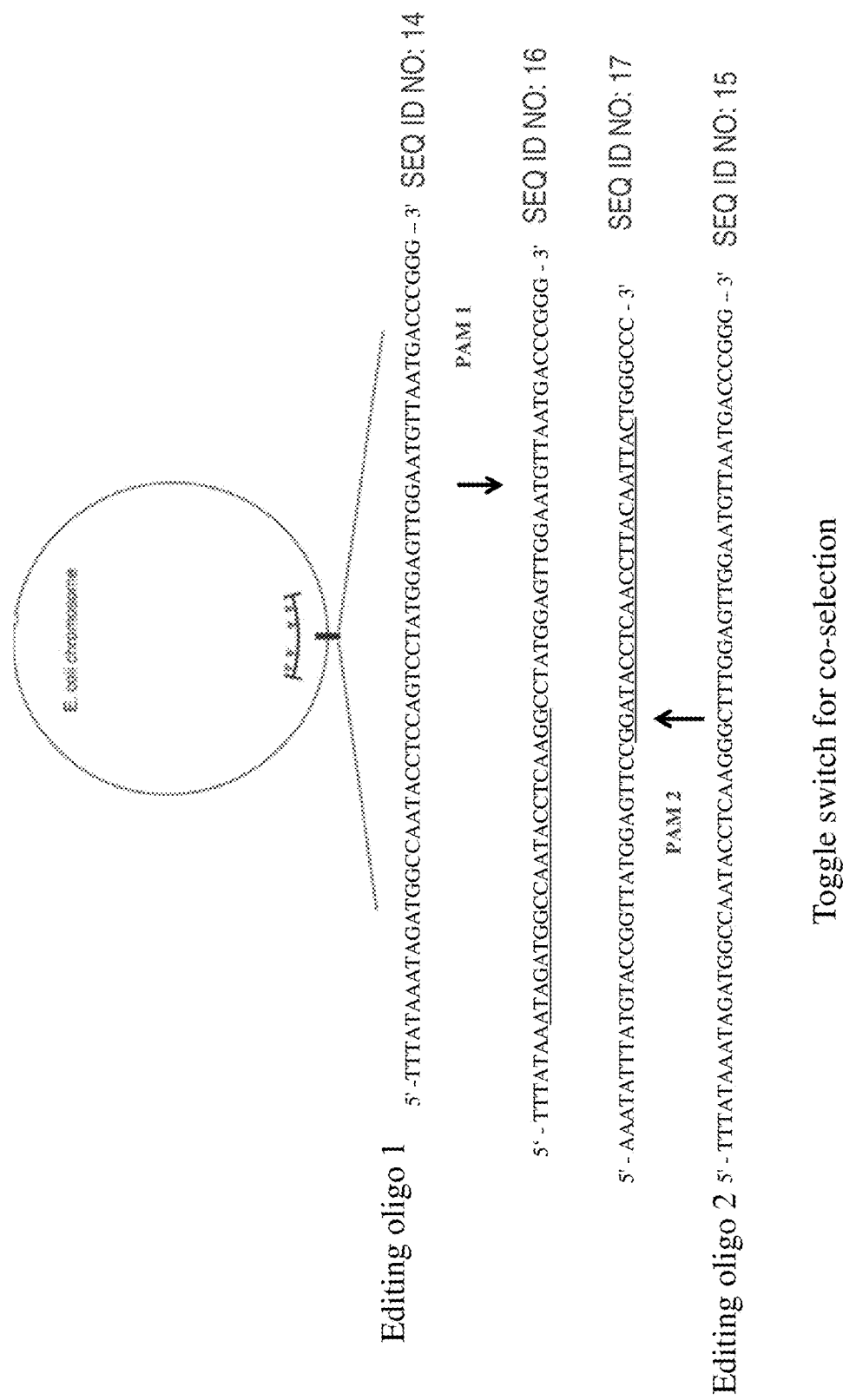
FIG. 8 shows strategies for iterative CRISPR co-selection.
Figure 9:
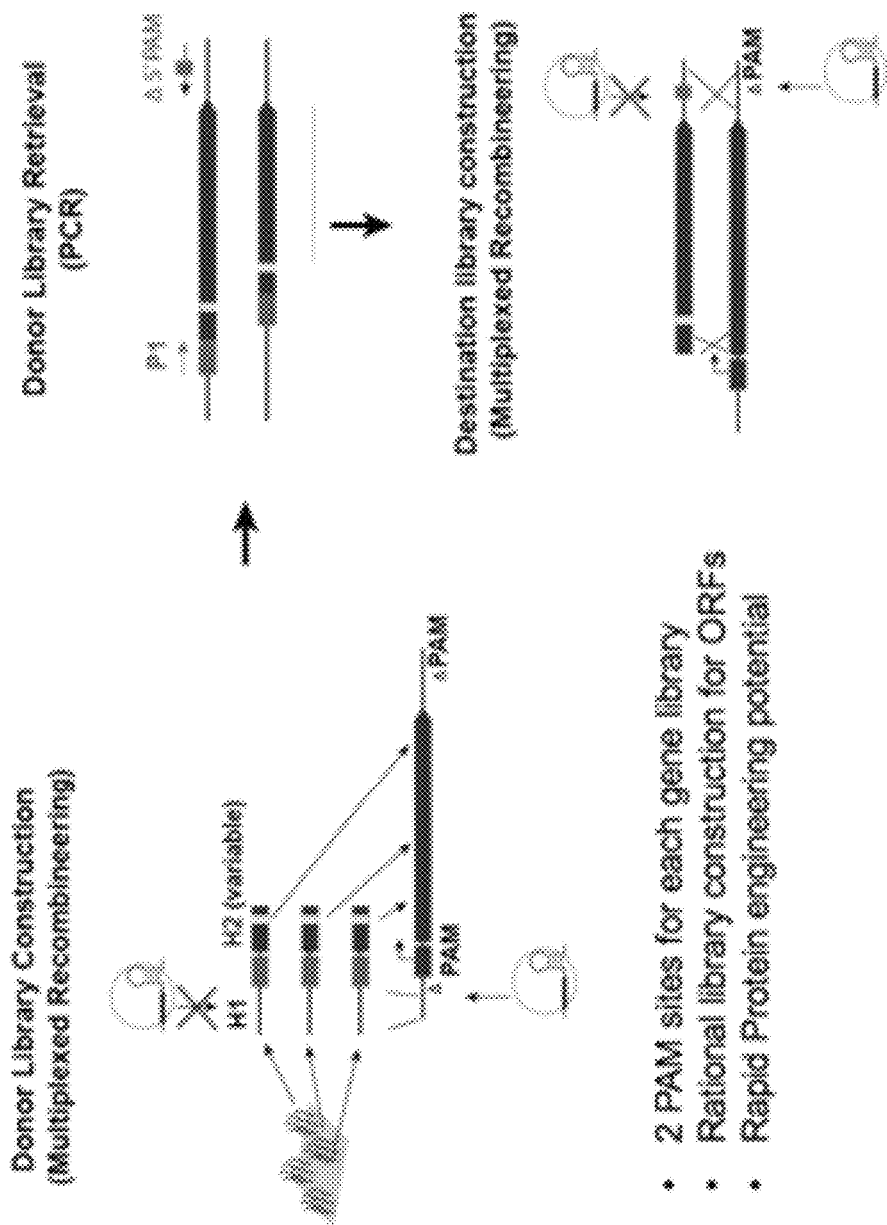
FIG. 9 presents a strategy for multiplexed protein engineering using CARPE.
Figure 10:
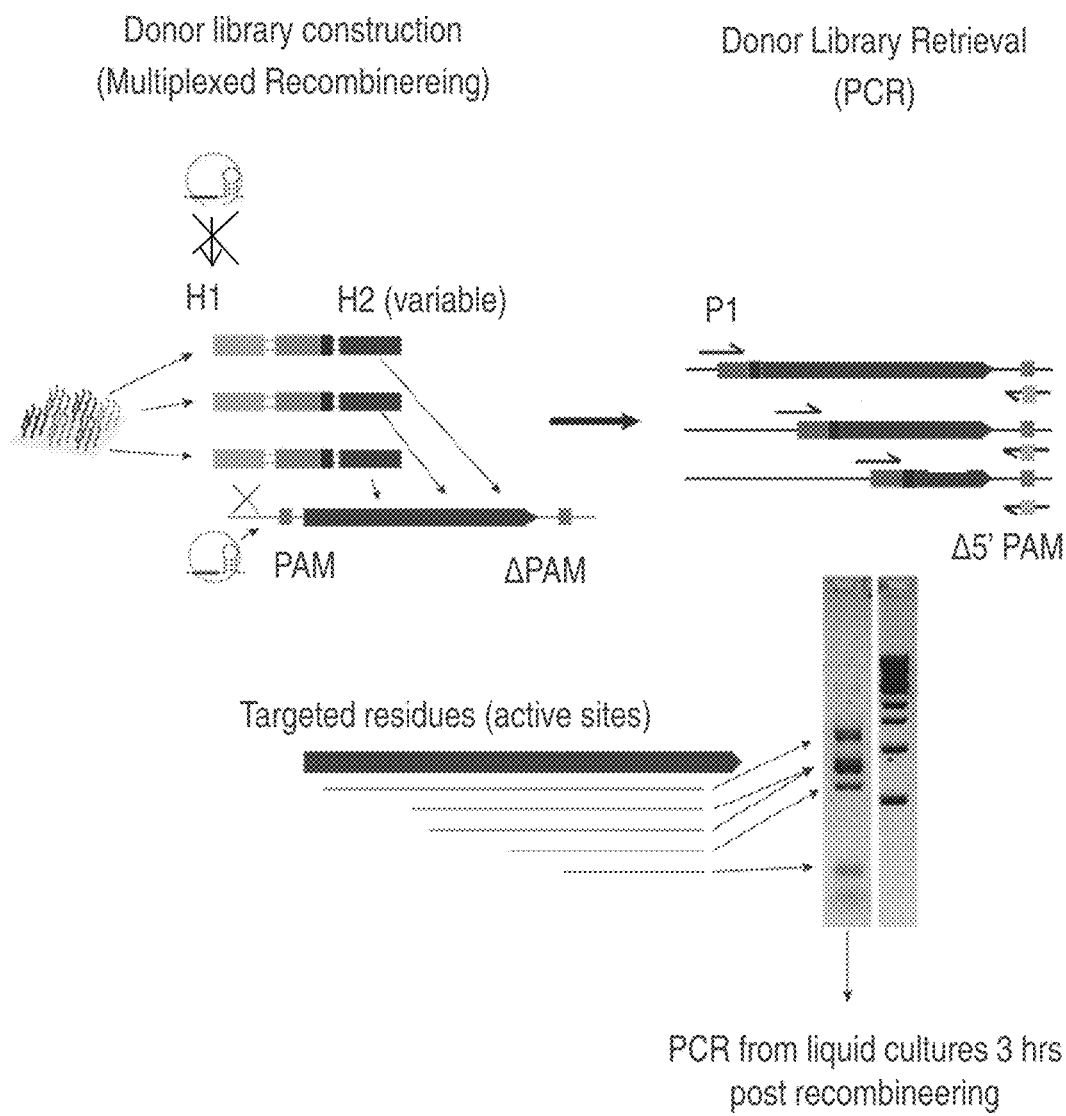
FIG. 10 shows construction of a galK donor library using CARPE.

In order to test the generality of the CARPE approach, the method was used, as described above, on a number of essential genes, including dxs, metA, and folA. Essential genes can be targeted using the gRNA design strategies (FIG. 3).

Data from CARPE experiments targeting the dxs gene also suggest that despite the gene disruption that occurs during the donor library creation, it is possible to effectively construct and retrieve the donor libraries within 1-3 hours post recombineering.

Example 3: Using the CARPE Method to Modulate Production of Isopentenol

The hunt for better biofuels for industrial manufacturing via bacterial production requires the ability to perform state of the art genome design, engineering, and screening for the desired product. Previously, we demonstrated the ability to individually modify the expression levels of every gene in the *E. coli* genome (Warner et al. *Nat. Biotechnol* (2010) 28:856-862). This method, termed trackable multiplex recombineering (TRMR), produced a library of about 8000 genomically-modified cells (~4000 over-expressed genes and ~4000 knocked down genes). This library was later screened under different conditions, which enabled deeper understanding of gene products' activities and resulted in better performing strains under these selections. TRMR allowed modification of protein expression for two levels (overexpressed and knocked down) but did not enable the modification of the open reading frame (ORF). Here, we aim to produce large libraries of ORF modifications and engineering whole metabolic pathways for the optimal production of biofuels.

A major difficulty in producing such libraries, which are rationally designed (in contrast to random mutagenesis), is the insertion efficiency of the desired mutations into the target cells. Recombineering, the canonical method for genome modifications in *E. coli*, uses recombinant genes from Lambda phage to facilitate the insertion of foreign DNA into the host genome. However, this process suffers from low efficiencies and may be overcome either by adding an antibiotic resistance gene followed by selection (as in TRMR), or by recursively inducing recombination events (i.e., by MAGE (Wang et al. *Nature* (2008) 460:894-898). The CARPE method described herein increases the recombineering efficiency involving the use of the CRISPR system to remove all non-recombinant cells from the population. CRISPR is a recently discovered RNA-based, adaptive defense mechanism of bacteria and archaea against invading phages and plasmids (Bhaya et al. *Ann. Rev. of Genetics* (2011) 45:273-297). This system underwent massive engineering to enable sequence-directed double strand breaks using two plasmids; one plasmid coding for the CRISPR-associated nuclease Cas9 and the second plasmid coding for the sequence-specific guide RNA (gRNA) that guides Cas9 to its unique location (Qi et al. *Cell* (2013) 45:273-297). The CARPE method utilizes the CRISPR system's ability to induce DNA breaks, and consequently cell death, in a sequence-dependent manner. We produced DNA recombineering cassettes that, in addition to the desired mutation within the ORF, include a mutation in a common location outside of the open reading frame of the gene which is targeted by the CRISPR machinery. This approach of linking/coupling desired mutations with the avoidance from CRISPR-mediated death, due to the PAM mutation/deletion, enables dramatic enrichment of the engineered cells within the total population of cells.

The method is further demonstrated using the DXS pathway. The DSX pathway results in the production of isopentenyl pyrophosphate (IPP) which results in the biosynthesis of terpenes and terpenoids. Interestingly, IPP can also be precursor of lycopene or isopentenol, given the addition of the required genes. While lycopene renders the bacterial colonies red, and hence is easily screenable, isopentenol is considered to be a 'second generation' biofuel with higher energy density and lower water miscibility than ethanol. Three proteins were selected for engineering: 1) DSX, the first and the rate-limiting enzyme of the pathway, 2) IspB, which diverts the metabolic flux from the DXS pathway, and 3) NudF, which has been shown to convert IPP to isopentenol in both *E. coli* and *B. subtilis* (Withers et al. *App. Environ. Microbiol* (2007) 73: 6277-6283; Zheng et al. *Biotechnol. for biofuels* (2013)6:57). Mutations in the genes encoding DXS and IspB will be screened for increased lycopene production with a new image analysis tool developed for colony color quantification. NudF activity will be assayed directly by measuring isopentenol levels by GC/MS and indirectly by isopentenol auxotrophic cells that will serve as biosensors. This method provides the ability to rationally engineer large mutational libraries into the *E. coli* genome with high accuracy and efficiency and a strain that produces high yield of isopentenol.

Example 4: Using the GEn-TraCER Method to Edit galK

Figure 12:
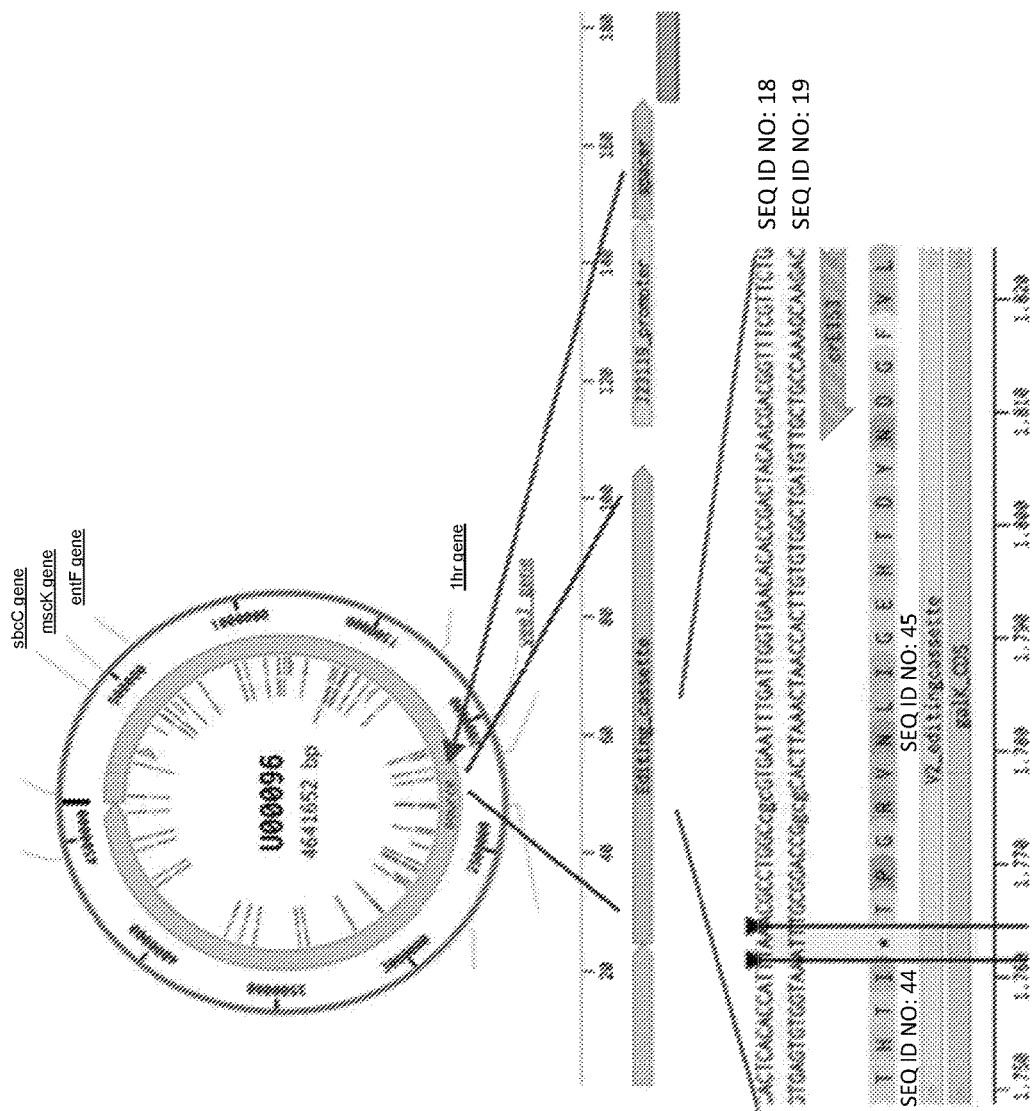
FIG. 12 shows a representative GEn-TraCER vector (construct) that includes an editing cassette for editing codon 24 of galK, a promoter, and spacer.

The GEn-TraCER method was used to edit the galK gene, which has served as a model system for recombineering in *E. coli* (Yu et al. 2000). The first GEn-TraCER cassettes constructed were designed to introduce a stop codon in place of an inframe PAM at codon 24 of galK, referred to as galK_Q24 (FIG. 12). Constructs and vectors were designed using a custom python script to generate the requisite mutations in high throughput.

Control cassettes were cloned into the gRNA vector described by Qi et al. *Cell* (2013) using a the Circular Polymerase cloning (CPEC) method. The backbone was linearized with the following primers: CCAGAAATCATC-CTTAGCGAAAGCTAAGGAT (SEQ ID NO: 29) and GTTTTAGAGCTAGAAATAGCAAGT-TAAAATAAGGCT (SEQ ID NO: 30).

GenTRACER cassettes were ordered as gblocks and amplified using the following primers: ATCACGAGGCA-GAATTTCAGATAAAAAAAATCCT-TAGCTTTCGCTAAGGATGATTTCTG G (SEQ ID NO: 31), ACTTTTTCAAGTTGATAACGGACTAGCCTT-ATTTTAACTTGCTATTTCTAGCTCTAAAAC (SEQ ID NO: 32).

The components were stitched together using CPEC and transformed into *E. coli* to generate the vectors. This procedure is to be performed in multiplex using the pooled oligonucleotide libraries with cloning efficiencies on the order of $10^4$-$10^5$ CFU/µg.

*E. coli* MG1655 cells carrying pSIM5 (lambda-RED plasmid) and the X2-cas9 plasmid were grown to mid log phase (0.4-0.7 OD) at 30° C. in LB with 50 µg/mL kanamycin and 34 μg/mL chloramphenicol. The recombineering functions of the pSIM5 vector were induced at 42° C. for 15 min and then placed on ice for 10 min. Cells were then made electrocompetent by pelleting and washing 2× with 10 mL chilled H2O. Cells were transformed with 100 ng of a GEn-TraCER plasmid (also encoding carbenicillin resistance) and recovered for 3 hrs at 37° C. 50-100 μL of cells were plated to the appropriate media containing 50 μg/mL kanamycin and 100 μg/ml carbenecillin to selectively enrich for the CRISPR-edited strains. Editing efficiencies for the galK gene were calculated using red/white screening on MacConkey agar supplemented with galactose.

Based on a screening on MacConkey agar editing efficiencies of ~100% were observed with the galK_Q24* design. Interestingly, unlike oligo-mediated recombineering methods that require mismatch repair knockouts to achieve high efficiency (Li et al. 2003; Sawitzke et al. 2011; Wang et al. 2011), there was no effect in strains with or without the mismatch repair machinery intact.

Chromosome and vector sequences were then verified by Sanger sequencing.

Figure 13:
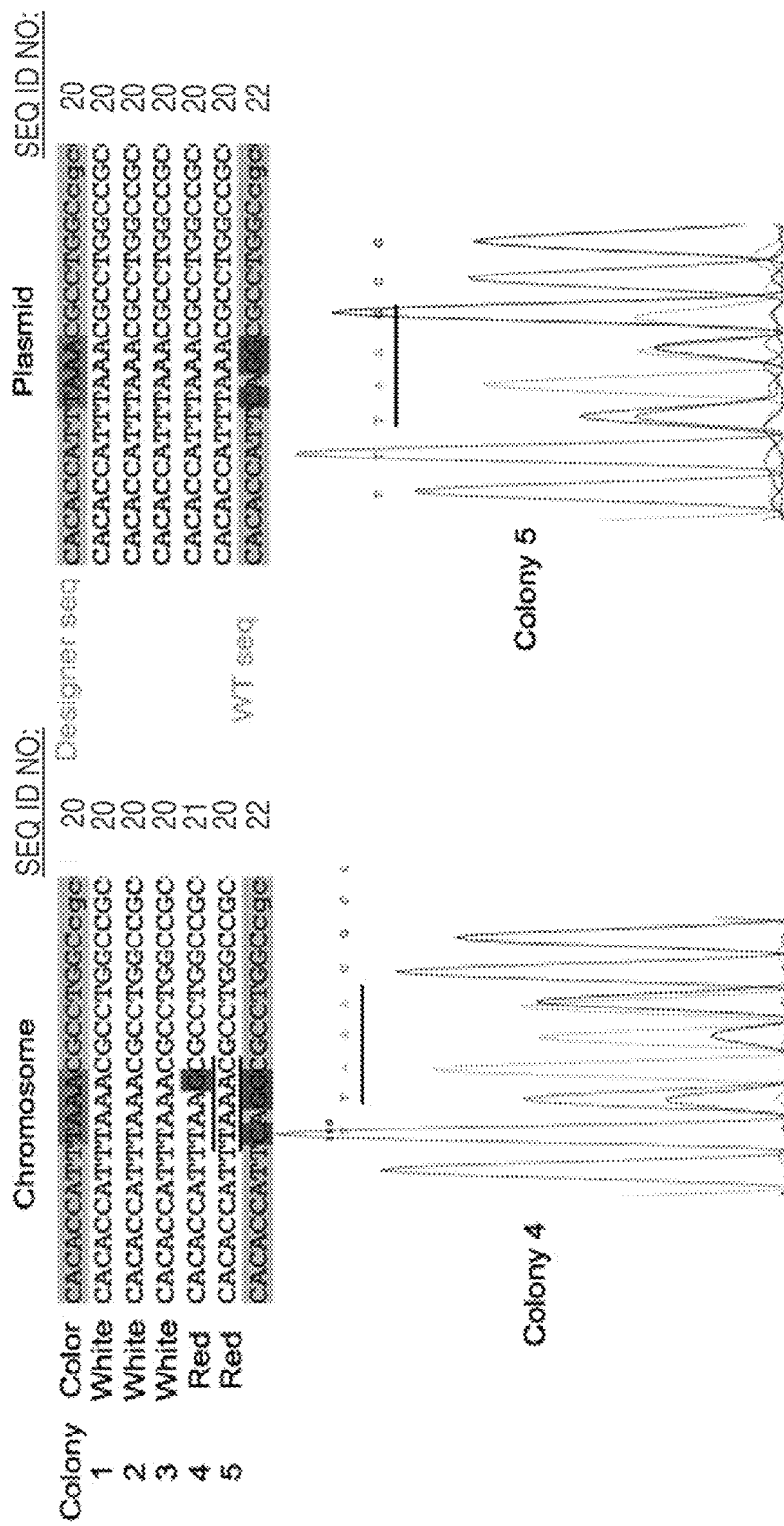
FIG. 13 shows the results of a galK editing using GEn-TraCER. The top panels show DNA sequencing results of the chromosome and vector (plasmid) from cells that had been transformed with the galK codon 24 editing GEn-TraCER vector, indicating the editing cassette (oligonucleotide) on the vector may be sequenced as a "trans-barcode" allowing high efficiency tracking of the desired genomic edit (mutation). The bottom panels show DNA sequencing chromatographs of cells that exhibit the unedited, wild-type phenotype (red). The method allows identification of cells with multiple chromosomes that carry both the wild-type, unedited allele and the edited/mutated allele.

As anticipated the designed mutation in the vector was mirrored on the chromosome (FIG. 13) indicating that the mutation was present in both locations and that the plasmid serves as a transacting barcode (trans-barcode) or record of the genome edit.

Figure 14A:
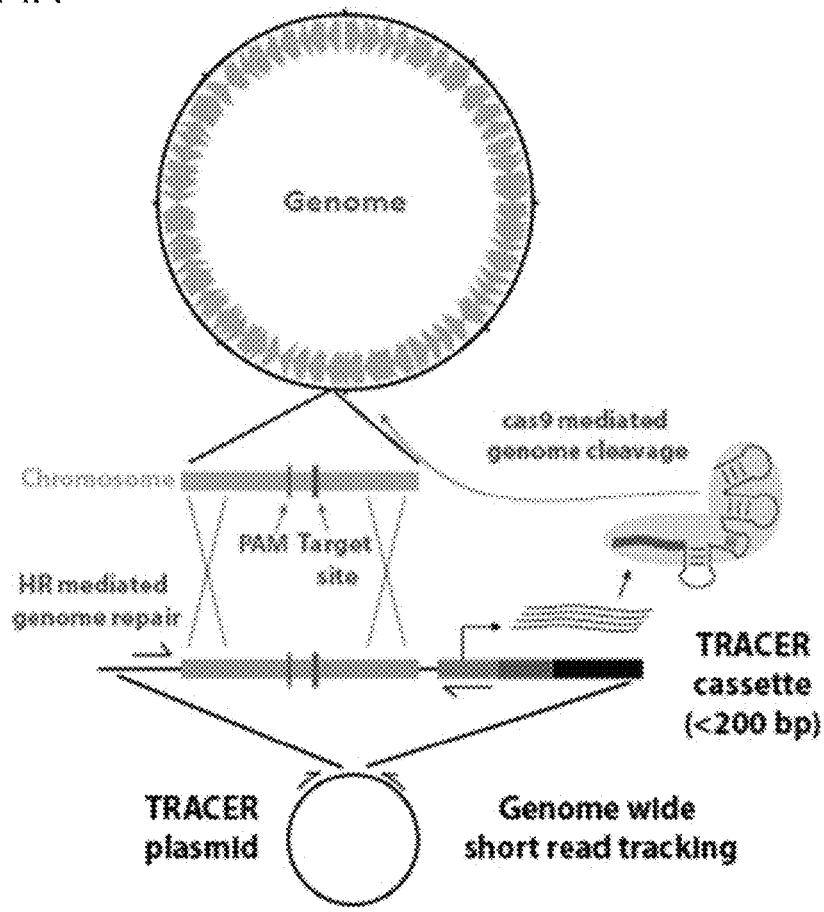
FIGS. 14A-14C show schematics of GEn-TraCER.
Figures 14B, 14C:
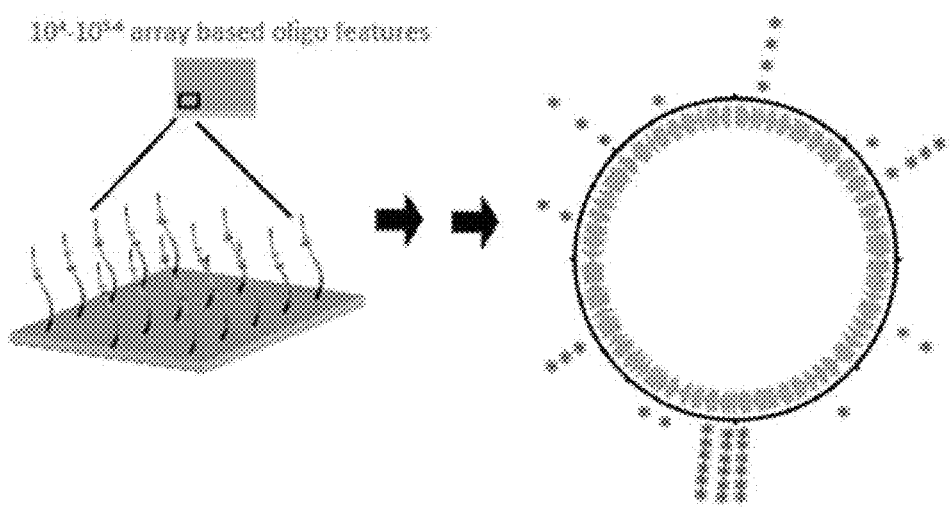
Figure 15A:
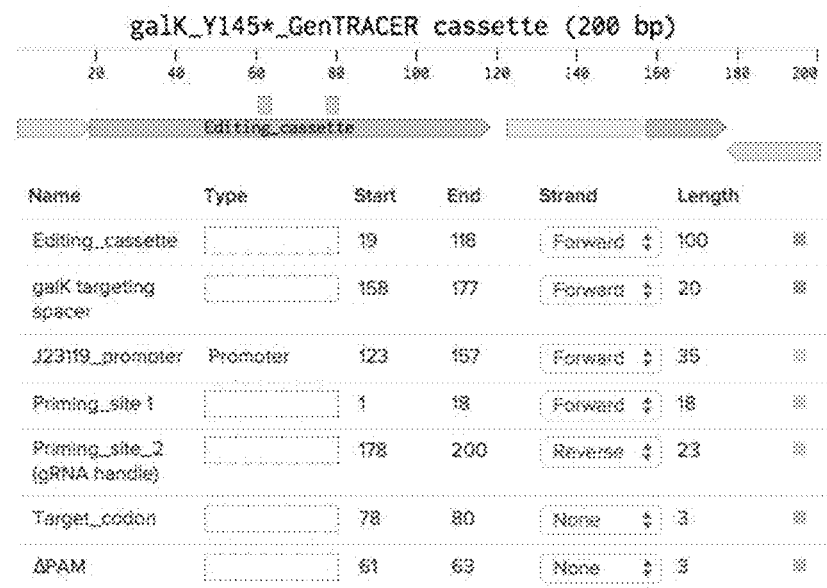
FIG. 15A shows an overview of GEn-TraCER vectors.
Figure 15B:
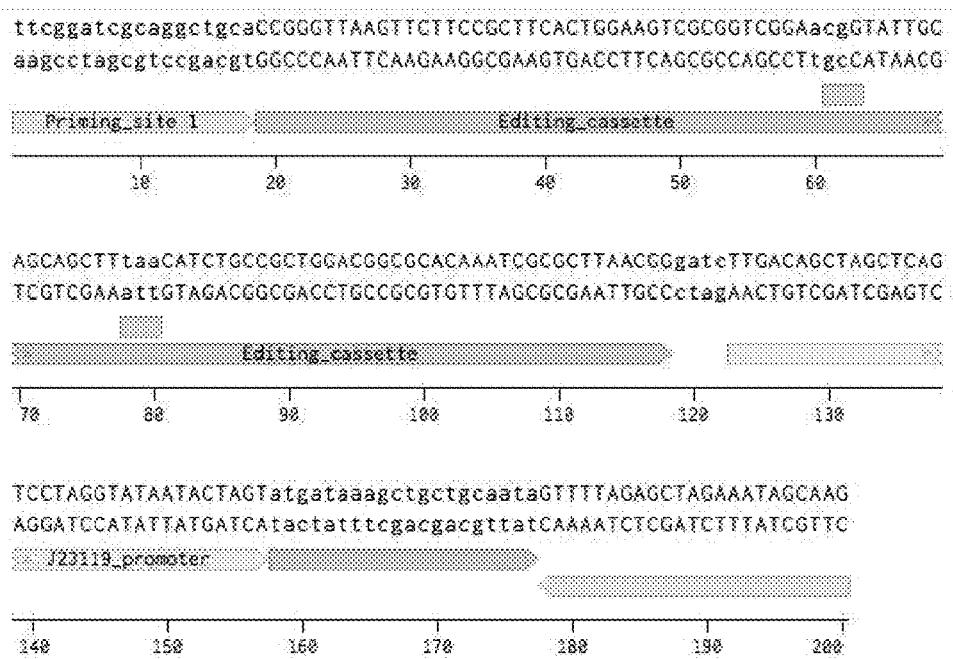
FIG. 15B shows a portion of a representative GEn-TraCER for generation of a Y145* mutation in the E. coli galK gene in which the PAM mutation and the codon that is mutated are separated by 17 nucleotides. The nucleic acid sequence of the portion of the representative GEn-TraCER is provided by SEQ ID NO: 28 and the reverse complement is provided by SEQ ID NO: 33.
Figure 16A:
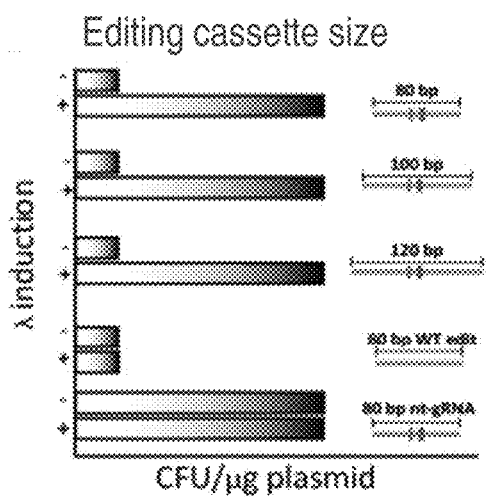
FIGS. 16A-16C present controls for GEn-TraCER design.
Figure 16B:
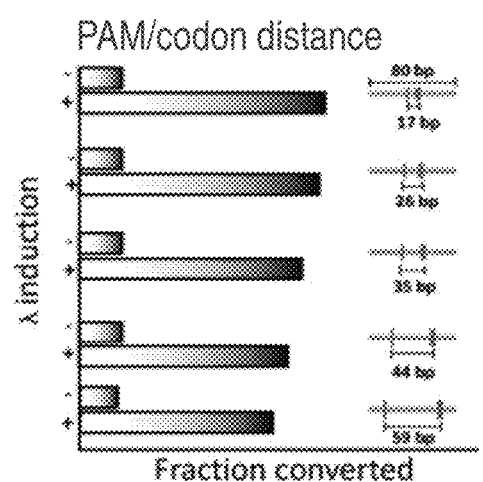
Figure 16C:
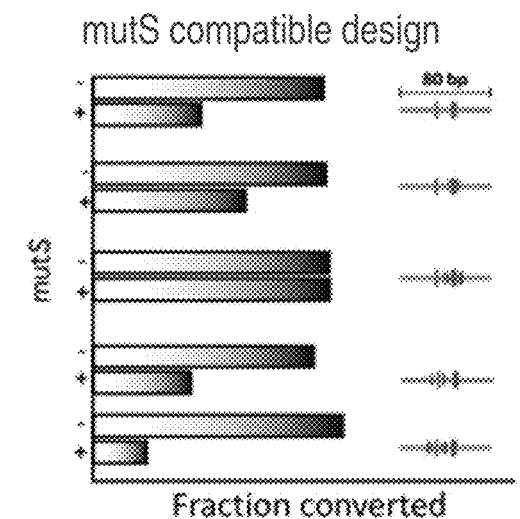

The design was adapted for rational mutagenesis of protein coding frames on a genome scale by generating "silent selectable scars" that consist of synonymous PAM mutation (FIG. 14B, ΔPAM) to "immunize" the cell against Cas9-mediated cleavage but leave the translation product unperturbed. We reasoned that silent scars may allow co-selection for nearby edits at a codon or other feature of interest with high efficiency. The effects of the homology arm length and the distance between the PAM mutation/deletion and the desired mutation in galK were assessed and the efficiencies compared (FIG. 16B). A significant increase in mutational efficiency at the galK position 145 was observed when the homology arm length was extended from 80 to 100 nucleotides (~5% and 45%, respectively) with identical PAM edits.

Example 5: Using the GEn-TraCER Method to Reconstruct Mutations

The GEn-TraCER approach was extended to a genomic scale using a custom automated design software that allows targeting of sites around the genome with a simple user input definition. The approach was tested by reconstructing all of non-synonymous point mutations from a recently reported study of thermal adaptation in *E. coli* (Tenaillon et al. 2012). This study characterized the complete set of mutations that occurred in 115 isolates from independently propagated strains. This dataset provides a diverse source of mutations whose individual fitness effects shed further light on the mechanistic underpinnings of this complex phenotype. Each of these mutations were reconstructed with a 2-fold redundancy in the codon usage and ΔPAM, where possible, to enable statistical correction for both the PAM and target codon mutations in downstream fitness analysis.

Example 6: Using the GEn-TraCER Method to Modulate Genetic Interactions

A promoter rewiring library is generated by integrating a promoter that is dynamically regulated by an environmental cue (oxygen level, carbon source, stress) upstream of each gene in the *E. coli* genome. Using the GEn-TraCER method, strains are generated with rewired genotypes that may be beneficial, for example for tolerance to chemicals of interest for production.

What is claimed is:

1. A library of at least two vectors, each vector comprising:
   (i) a nucleic acid encoding a guide RNA (gRNA) comprising a region complementary to a target region of a nucleic acid in one or more cells covalently linked to
   (ii) an editing cassette comprising
       (a) a region homologous to the target region in the one or more cells with a mutation of at least one nucleotide relative to the target region in the one or more cells, and
       (b) a protospacer adjacent motif (PAM) mutation;
   wherein the at least two vectors have different mutations relative to the target region in the one or more cells.

2. The library of claim 1, wherein at least one of the vectors encoding a gRNA further comprises a region that interacts with, or recruits, a Cas9 endonuclease.

3. The library of claim 1, wherein the target region in the one or more cells is within a non-coding region.

4. The library of claim 1, wherein the target region in the one or more cells is within a gene of interest within the one or more cells.

5. The library of claim 4, wherein the mutation of at least one nucleotide is within at least one codon of the gene of interest.

6. The library of claim 5, wherein the mutation of at least one codon is within 100 nucleotides of the PAM mutation.

7. The library of claim 4, wherein the PAM mutation is outside of a reading frame of the gene of interest.

8. The library of claim 4, wherein the gene of interest is a prokaryotic gene.

9. The library of claim 4, wherein the gene of interest is a eukaryotic gene.

10. The library of claim 1, wherein in at least one of the vectors the gRNA comprises a single chimeric gRNA.

11. The library of claim 1, wherein the library of vectors comprises at least 27,000 different editing cassettes.

12. The library of claim 1, wherein the library of vectors comprises about $10^4$-$10^6$ different editing cassettes.

13. The library of claim 1, wherein the library of vectors comprises at least $10^4$ different editing cassettes.

14. The library of claim 1, wherein the library of vectors comprises at least $10^5$ different editing cassettes.

15. The library of claim 1, wherein the library of vectors comprises at least $10^6$ different editing cassettes.

16. The library of claim 1, wherein the library of vectors comprises linear vectors.

17. The library of claim 1, wherein the library of vectors comprises circular vectors.

18. A library comprising a plurality vectors, wherein each vector comprises:
   (i) an editing cassette comprising:
       (a) a region homologous to a target region in one or more cells with a mutation of at least one nucleotide relative to the target region in the one or more cells, and
       (b) a first protospacer adjacent motif (PAM) mutation; and
   (ii) a nucleic acid encoding a guide RNA (gRNA) complementary to the target region of the one or more cells, wherein the editing cassette is covalently linked to the nucleic acid encoding the guide RNA, and wherein the plurality of vectors have different mutations relative to the target region in the one or more cells.

19. The library of claim 18, wherein said nucleic acid encoding a gRNA further comprises a region that interacts with, or recruits, a Cas9 endonuclease.

20. The library of claim 18, wherein the target region of at least one of the plurality of vectors is within a non-coding region.

21. The library of claim 18, wherein the target region of at least one of the plurality of vectors is within a gene of interest within the one or more cells.

22. The library of claim 21, wherein at least one of the plurality of vectors comprises a mutation of at least one nucleotide within at least one codon of the gene of interest.

23. The library of claim 22, wherein the mutation of at least one codon is within 100 nucleotides of the PAM mutation.

24. The library of claim 21, wherein the PAM mutation is outside of a reading frame of the gene of interest.

25. The library of claim 21, wherein the gene of interest is a prokaryotic gene.

26. The library of claim 21, wherein the gene of interest is a eukaryotic gene.

27. The library of claim 18, wherein at least one of the gRNAs comprises a single chimeric gRNA.

28. The library of claim 18, wherein the library of vectors comprises at least 27,000 different editing cassettes.

29. The library of claim 18, wherein the library of vectors comprises about $10^4$-$10^6$ different editing cassettes.

30. The library of claim 18, wherein the library of vectors comprises at least $10^4$ different editing cassettes.

31. The library of claim 18, wherein the library of vectors comprises at least $10^5$ different editing cassettes.

32. The library of claim 18, wherein the library of vectors comprises at least $10^6$ different editing cassettes.

33. The library of claim 18, wherein the library of vectors comprises linear vectors.

34. The library of claim 18, wherein the library of vectors comprises circular vectors.

* * * * *

UNITED STATES PATENT AND TRADEMARK OFFICE
CERTIFICATE OF CORRECTION

PATENT NO. : 10,240,167 B2
APPLICATION NO. : 15/948789
DATED : March 26, 2019
INVENTOR(S) : Ryan T. Gill and Andrew Garst It is certified that error appears in the above-identified patent and that said Letters Patent is hereby corrected as shown below:

On the Title Page

Item (73) Assignee:
Remove "Inscripta, Inc., Boulder, CO (US)" and insert --THE REGENTS OF THE UNIVERSITY OF COLORADO, A BODY CORPORATE, DENVER, CO (US)--

Signed and Sealed this
Seventh Day of April, 2020

Andrei Iancu
*Director of the United States Patent and Trademark Office*

SEQUENCE LISTING

<160> NUMBER OF SEQ ID NOS: 45

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ccgtggatcc taggctggtc tc                                            22

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gcctggctaa gtgaatt                                                  17

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 3
agcaaaaaca ggtatta                                                17

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aaacaggtat taaagag                                                17

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gcctggccgc gtgaatt                                                17

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccagtttcaa ggctgta                                                17

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ccagtttgta ggctgta                                                17

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cttcaaacgt accctgg                                                17

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 9
agccaaaaat aggtatt                                                      17

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gcctggccgc gtgaatt                                                      17

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cttcaaaagg accctgg                                                      17

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cttcaaaaca accctgg                                                      17

<210> SEQ ID NO 13
<211> LENGTH: 1052
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (325)..(325)
<223> OTHER INFORMATION: a, c, t or g
<220> FEATURE:
<221> NAME/KEY: modified_base
<222> LOCATION: (632)..(632)
<223> OTHER INFORMATION: a, c, t or g
<220> FEATURE:
<221> NAME/KEY: modified_base
<222> LOCATION: (806)..(806)
<223> OTHER INFORMATION: a, c, t or g
<220> FEATURE:
<221> NAME/KEY: modified_base
<222> LOCATION: (892)..(892)
<223> OTHER INFORMATION: a, c, t or g
<220> FEATURE:
<221> NAME/KEY: modified_base
<222> LOCATION: (985)..(985)
<223> OTHER INFORMATION: a, c, t or g

<400> SEQUENCE: 13
cggaaccggt attgcagcag ctttatcatc tgccgctgga cggcgcacaa atcgcgctta       60
acggtcagga agaacctcgt gaatcgcatc tccgcaacgc caatgacact ccgccagcag      120
aacgcggcgt tggtatggtg tttcagtctt acgcgctcta tccccacctg tcagtagcag      180
```

```
aaaacatgtc atttggcctg aaactggcaa gcacgcccgg tagcagagcc cgagtattac    240
atcgaactgg atttcaacag cggtaagatc cttgagagtt ttcgcccccga agaacgtttt   300 ccaatgatga gcacttttaa agttntgcta tgtggcgcgg acggtttggg cgaggatgtt    360
cgggactgag cgtatggaag agcacttgcg ttttgccgcc tgctactggc acaccttctg    420
ctggaacggg gcggatatgt ttttcagatt gggttgcgag tggtgggcga cggttttatg    480
attgcaggtc cgctgggcgg ctggtgcatt aagcacttcg accgctgggt agacggtaag    540
atcaaatgcc gattgtcagt tggagggagc aagggaacca gatcaaacca gagcacttca    600
aaaactgggt tgaatgggcg aaagccaatc anctcggtct ggatccaacc atgcgtatcg    660
tgccaagtgc gtcccagaca acaagtatat gaattatcgg aggttgtcga tcaactcgat    720
atacccgtac tttgttatgg tttacgtacc gattttcgag gtgaattatt tattggcagc    780
ccccgttgtg gtgtccttct gatganccca ttacaggcac gcttgagcca ggacctggcg    840
cgcgagcaaa ttcgccaggc gcaggatggt cacttaccga cttgcaactt ancccgctgt    900
tcccgaggac gttaacgcgc tggtcgatga gtacaaaagc tgctacacca tgacgccttg    960
cataggagcc acgaaccgcc atacnagaca ttttgaggca tttcagtcag ttgctcaatg    1020
tacctatacc cagaccgttc agctggatat ta                                  1052

<210> SEQ ID NO 14
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tttataaata gatggccaat acctccagtc ctatggagtt ggaatgttaa tgacccggg     59

<210> SEQ ID NO 15
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tttataaata gatggccaat acctcaaggg ctttggagtt ggaatgttaa tgacccggg     59

<210> SEQ ID NO 16
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tttataaata gatggccaat acctcaaggc ctatggagtt ggaatgttaa tgacccggg     59

<210> SEQ ID NO 17
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 17
aaatatttat gtaccggtta tggagttccg gatacctcaa ccttacaatt actgggccc    59

<210> SEQ ID NO 18
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cactcacacc atttaaacgc ctggccgcgt gaatttgatt ggtgaacaca ccgactacaa    60
cgacggtttc gttctg                                                   76

<210> SEQ ID NO 19
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cagaacgaaa ccgtcgttgt agtcggtgtg ttcaccaatc aaattcacgc ggccaggcgt    60
ttaaatggtg tgagtg                                                   76

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cacaccattt aaacgcctgg ccgc                                          24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
cacaccattt aagcgcctgg ccgc                                          24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cacaccattc aggcgcctgg ccgc                                          24

<210> SEQ ID NO 23
<211> LENGTH: 45
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 23
ggaaccgtat tgcagcagct ttatcatctg ccgctggacg gcgca              45

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Thr Val Leu Gln Gln Leu Tyr His Leu Pro Leu Asp Gly Ala
1               5                   10                  15

<210> SEQ ID NO 25
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ggaacggtat tgcagcagct ttaacatctg ccgctggacg gcgca              45

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Thr Val Leu Gln Gln Leu
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

His Leu Pro Leu Asp Gly Ala
1               5

<210> SEQ ID NO 28
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
ttcggatcgc aggctgcacc gggttaagtt cttccgcttc actggaagtc gcggtcggaa      60
cggtattgca gcagctttaa catctgccgc tggacggcgc acaaatcgcg cttaacggga     120
```

```
tcttgacagc tagctcagtc ctaggtataa tactagtatg ataaagctgc tgcaatagtt    180
ttagagctag aaatagcaag                                                200
```

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

```
ccagaaatca tccttagcga aagctaagga t                                   31
```

<210> SEQ ID NO 30
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

```
gttttagagc tagaaatagc aagttaaaat aaggct                              36
```

<210> SEQ ID NO 31
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31

```
atcacgaggc agaatttcag ataaaaaaaa tccttagctt tcgctaagga tgatttctgg    60
```

<210> SEQ ID NO 32
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

```
acttttcaa gttgataacg gactagcctt attttaactt gctatttcta gctctaaaac     60
```

<210> SEQ ID NO 33
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
cttgctattt ctagctctaa aactattgca gcagctttat catactagta ttatacctag    60
gactgagcta gctgtcaaga tcccgttaag cgcgatttgt gcgccgtcca gcggcagatg   120
ttaaagctgc tgcaataccg ttccgaccgc gacttccagt gaagcggaag aacttaaccc   180
ggtgcagcct gcgatccgaa                                               200
```

```
<210> SEQ ID NO 34
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34 acgaaa                                                                     6

<210> SEQ ID NO 35
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35 actgggttg                                                                  9

<210> SEQ ID NO 36
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36 ttatcatc                                                                   8

<210> SEQ ID NO 37
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cccgaagaac                                                                10

<210> SEQ ID NO 38
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38 cattaagca                                                                  9

<210> SEQ ID NO 39
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39 gctactggc                                                                  9
```

```
<210> SEQ ID NO 40
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40 cttacgcgc                                                                     9

<210> SEQ ID NO 41
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41 ccgtacttt                                                                     9

<210> SEQ ID NO 42
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42 ttcgccagg                                                                     9

<210> SEQ ID NO 43
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43 tcaatg                                                                        6

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Thr His Thr Ile
1

<210> SEQ ID NO 45
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 45

Thr Pro Gly Arg Val Asn Leu Ile Gly Glu His Thr Asp Tyr Asn Asp
1               5                   10                  15

Gly Phe Val Leu
            20
```